(12) United States Patent
Kinder, Jr. et al.

(10) Patent No.: US 6,239,127 B1
(45) Date of Patent: May 29, 2001

(54) CERTAIN SUBSTITUTED CAPROLACTAMS, PHARMACEUTICAL COMPOSITIONS CONTAINING THEM AND A PROCESS FOR THEIR PREPARATION

(75) Inventors: Frederick Ray Kinder, Jr., Morristown; Kenneth Walter Bair, Mountain Lakes; Christopher Turchik Jagoe, Chatham; Richard William Versace, Wanaque; Sompong Wattanasin, Hopatcong, all of NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/441,739

(22) Filed: Nov. 17, 1999

(51) Int. Cl.$^7$ ................. C07D 223/10; C07D 409/12; C07D 403/12; A61K 31/55; A61P 35/00

(52) U.S. Cl. ................. 514/212.03; 514/212.08; 540/524; 540/526

(58) Field of Search ................. 540/524, 526; 514/212.08, 212.03

(56) References Cited

U.S. PATENT DOCUMENTS 4,831,135  5/1989  Crews et al. ................. 540/526

FOREIGN PATENT DOCUMENTS 687673  12/1995  (EP).

OTHER PUBLICATIONS

McDougal P. et al., J.Org.Chem., vol. 51 pp. 4494–4497 (1986).
Adamczeski M. et al., J.Am.Chem.Soc., Vol. 111, pp. 647–654 (1989).
Adamczeski M. et al., J.Org.Chem. vol. 55, pp. 240–242 (1990).
Valeria D'Auria, M. et al., J.Nat.Prod. vol. 60, pp. 814–816 (1997).
Mukai C. et al., J.Chem.Soc. Perkin Trans., vol. 1, Issue 22, pp. 2849–2854 (1995).
Mukai C. et al., J.Org.Chem., vol. 60, pp. 5910–5918 (1995).
Chida N. et al., Heterocycles, vol. 38, No. 11, pp. 2383–2388 (1994).
Mukai C. et al., Tetrahedron Letters, vol. 35, No. 37, pp. 6899–69002 (1994).
Marshall J.A. et al., Synlett, Issue 12, pp. 1007–1008 (1992).
Chida N et al., J.Chem.Soc., Chem.Commun., Issue 15, pp. 1064–1066 (1992).
Kishimoto H. et al., J.Org.Chem., vol. 57, pp. 5042–5044 (1992).
Broka C.A. et al., Tetrahedron Letters, vol. 32, No. 42, pp. 5907–5910 (1991).

Gurjar M.K. et al., Tetrahedron Letters, vol. 32, No. 28, pp. 3409–3412 (1991).
Chida N. et al., Tetrahedron Letters. vol. 32, No. 8, pp. 1063–1066 (1991).
Rudi A., et al., Journal of Natural Products, vol. 57, No. 6, pp. 829–832 (1994).
Fernandez R., et al., Journal of Natural Products, vol. 62, No. 5, pp. 678–680 (1999).

*Primary Examiner*—Bruck Kifle
(74) *Attorney, Agent, or Firm*—Joseph J. Borovian

(57) ABSTRACT

The present invention relates to certain substituted caprolactam compounds of formula (I), where $R_1$ is $(C_{1-6})$alkyl or $(C_{3-6})$cycloalkyl; $R_2$ hydrogen or $(C_{1-6})$alkyl; X is $(C_{1-12})$alkynylene; $(C_{2-12})$alkynylene; m is 0 or 1; and $R_3$ is $(C_{3-8})$cycloalkyl; or an aromatic ring system selected from (II, III, IV and V), where $R_4$ is hydrogen, chloro, or methoxy; $R_5$ is hydrogen, chloro, $(C_{1-18})$alkyl or $(C_{1-18})$alkoxy, and Z is oxygen, sulfur, N—H, or N—CH$_3$; or a pharmaceutically acceptable acid addition salt thereof, where possible, pharmaceutical compositions containing said compounds, the use of said compounds in treating tumors and to a process for making said compounds.

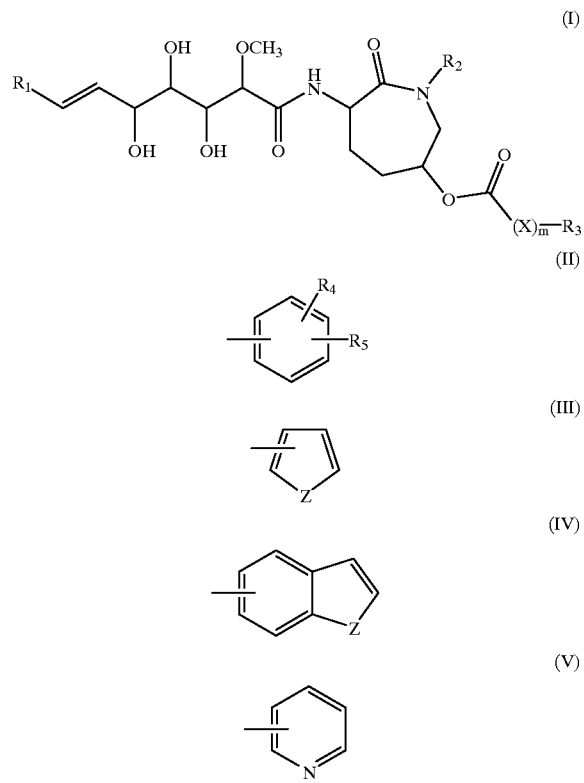

11 Claims, No Drawings

CERTAIN SUBSTITUTED CAPROLACTAMS, PHARMACEUTICAL COMPOSITIONS CONTAINING THEM AND A PROCESS FOR THEIR PREPARATION

This application claims the benefit of U.S. application Ser. No. 09/193,354, and which is incorporated herein by reference.

The present invention relates to the area of chemotherapeutic agents and, more particularly, relates to certain substituted caprolactams, pharmaceutical compositions comprising said caprolactams, a method of treating tumors, the use of said caprolactams in the chemotherapy of tumors, and a process for preparing said compounds.

Cancer is a serious health problem throughout the world. As a result, an extensive number of research endeavors has been undertaken in an effort to develop therapies appropriate to the treatment and alleviation of cancer in humans.

In the chemotherapeutic area, research has been conducted to develop anti-tumor agents effective against various types of cancer. Oftentimes, anti-tumor agents which have been developed and found effective against cancer cells are, unfortunately, also toxic to normal cells. This toxicity manifests itself in weight loss, nausea, vomiting, hair loss, fatigue, itching, hallucinations, loss of appetite, etc., upon administration of the anti-tumor agent to a patient in need of cancer chemotherapy.

Furthermore, conventionally used chemotherapeutic agents do not have the effectiveness desired or are not as broadly effective against different types of cancers as desired. As a result, a great need exists for chemotherapeutic agents which are not only more effective against all types of cancer, but which have a higher degree of selectivity for killing cancer cells with no or minimal effect on normal healthy cells. In addition, highly effective and selective anti-tumor agents, in particular, against cancers of the colon, bladder, prostate, stomach, pancreas, breast, lung, liver, brain, testis, ovary, cervix, skin, vulva and small intestine are desired. Moreover, anti-tumor activity against colon, breast, lung and prostate cancers as well as melanomas are particularly desired because of the lack of any particular effective therapy at the present time.

The present invention provides new anti-tumor agents which are effective against a variety of cancer cells. More particularly, the present invention relates to certain substituted caprolactams which exhibit a high degree of selectivity in killing cancer cells. The essence of the instant invention is the finding that certain substituted caprolactams are useful in treating tumors.

The invention relates to caprolactams of formula I:

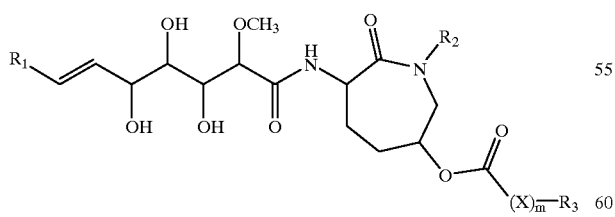

I where
$R_1$ is $(C_{1-6})$alkyl or $(C_{3-6})$cycloalkyl;
$R_2$ is hydrogen or $(C_{1-6})$alkyl;
X is $(C_{1-12})$ alkylene; $(C_{2-12})$ alkenylene; or $(C_{2-12})$ alkynylene;
m is 0 or 1; and
$R_3$ is $(C_{3-8})$cycloalkyl; or an aromatic ring system selected from II, III, IV and V:

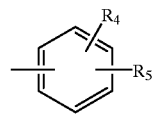

II

III

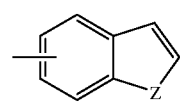

IV

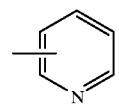

V where
$R_4$ is hydrogen, chloro, or methoxy;
$R_5$ is hydrogen, chloro, $(C_{1-18})$alkyl or $(C_{1-18})$alkoxy; and
Z is oxygen, sulfur, N—H, or N—CH$_3$;

or a pharmaceutically acceptable acid addition salt thereof, where possible.

Preferred compounds of formula I are those where $R_1$ is $(C_{1-6})$ alkyl;
$R_2$ is hydrogen or $(C_{1-4})$ alkyl;
X is $(C_{1-6})$ alkylene or $(C_{2-6})$ alkenylene;
m is 0 or 1; and
$R_3$ is $(C_{3-8})$cycloalkyl; or an aromatic ring system selected from II, III, IV and V where
$R_4$ is hydrogen, chloro, or methoxy;
$R_5$ is hydrogen, chloro, $(C_{1-18})$alkyl or $(C_{1-18})$alkoxy; and Z is oxygen, sulfur, N—H, or N—CH$_3$;
or a pharmaceutically acceptable acid addition salt thereof, where possible.

More preferred compounds are those of formula I where $R_1$ is i-propyl or t-butyl;
$R_2$ is hydrogen or methyl;
m is 0 or 1;
X is $(C_{1-6})$ alkylene; and
$R_3$ is $(C_{5-7})$cycloalkyl; or an aromatic ring system selected from IIa and V:

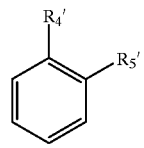

IIa

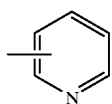

where
R₄'is in the meta position and is hydrogen or chloro; and
R₅'is in the para position and is hydrogen, chloro, ($C_{1-18}$) alkyl or ($C_{1-18}$)alkoxy;
or a pharmaceutically acceptable acid addition salt thereof, where possible.

Even more preferred compounds are those of formula I where $R_1$ is i-propyl or t-butyl;

$R_2$ is hydrogen or methyl;

m is 0 or 1;

X is methylene or ethylene; and $R_3$ is ($C_{5-7}$)cycloalkyl, phenyl, 3,4-dichlorophenyl, 4-methoxyphenyl, 4-n-decylphenyl, 4-n-decyloxyphenyl or 3-pyridyl;

with the proviso that when m is 0, $R_3$ is ($C_{5-7}$)cycloalkyl, 4-n-decylphenyl or 4-n-decyloxyphenyl;

or a pharmaceutically acceptable acid addition salt thereof, where possible.

In another embodiment, the instant invention provides pharmaceutical compositions, especially for the treatment of tumors in warm-blooded animals, comprising a pharmaceutically acceptable carrier or diluent and a antitumorally effective dose of a compound of formula I above, preferably 3,4,5-trihydroxy-2-methoxy-8,8-dimethyl-N-[hexahydro-2-oxo-6-(cyclohexylcarbonyl)oxy-2H-azepin-3-yl]non-6-enamide or 3,4,5-trihydroxy-2-methoxy-8,8-dimethyl-N-[hexahydro-2-oxo-6-(1-oxo-3-phenylpropoxy)-2H-azepin-3-yl]non-6-enamide, or a pharmaceutically acceptable acid addition salt thereof, where possible.

In still another embodiment, the instant invention provides a method for treating tumors comprising administering to a mammal in need of such treatment a therapeutically effective amount of a compound of formula I above, or a pharmaceutically acceptable acid addition salt thereof, where possible.

In another embodiment, the instant invention relates to the use of a compound of formula I or of a pharmaceutically acceptable salt of such a compound for the preparation of a pharmaceutical composition for use in the chemotherapy of tumors.

Furthermore, the instant invention relates to the use of a compound of formula I or of a pharmaceutically acceptable salt of such a compound for the chemotherapy of tumors.

In the above definitions: 1) the alkyl groups containing 1 to 6 carbon atoms are either straight or branched chain, of which examples of the latter include isopropyl, isobutyl, t-butyl, isopentyl, neopentyl, isohexyl, 3-methylpentyl, 2,2-dimethylbutyl, 2,3-dimethylbutyl and 1,1,2,2-tetramethylethyl; and 2) the alkyl and alkoxy groups containing 1 to 18 carbon atoms are either straight or branched chain.

The term "($C_{1-12}$) alkylene" as used herein refers to a straight or branched chain divalent group consisting solely of carbon and hydrogen and having from 1 to 12 carbon atoms. Examples of "alkylene" groups include methylene, ethylene, propylene, butylene, pentylene, 3-methypentylene, etc.

The term "($C_{2-12}$) alkenylene" as used herein refers to a straight or branched chain divalent group consisting solely of carbon and hydrogen, containing at least one carbon-carbon double bond, and having from 2 to 12 carbon atoms. Examples of "alkenylene" groups include ethenylene, propenylene, butenylene, pentenylene, 3-methylpentenylene, etc.

The term "($C_{2-12}$) alkynylene" as used herein refers to a straight or branched chain divalent group consisting solely of carbon and hydrogen, containing at least one carbon-carbon triple bond, and having from 2 to 12 carbon atoms. Examples of "alkynylene" groups include acetylene, propynylene, butynylene, pentynylene, 3-methylpentynylene, etc.

The acid addition salts of the compounds of formula I may be those of pharmaceutically acceptable organic or inorganic acids. Although the preferred acid addition salts are those of hydrochloric and methanesulfonic acid, salts of sulfuric, phosphoric, citric, fumaric, maleic, benzoic, benzenesulfonic, succinic, tartaric, lactic and acetic acid may also be utilized.

The caprolactams of formula I may be prepared as depicted below:

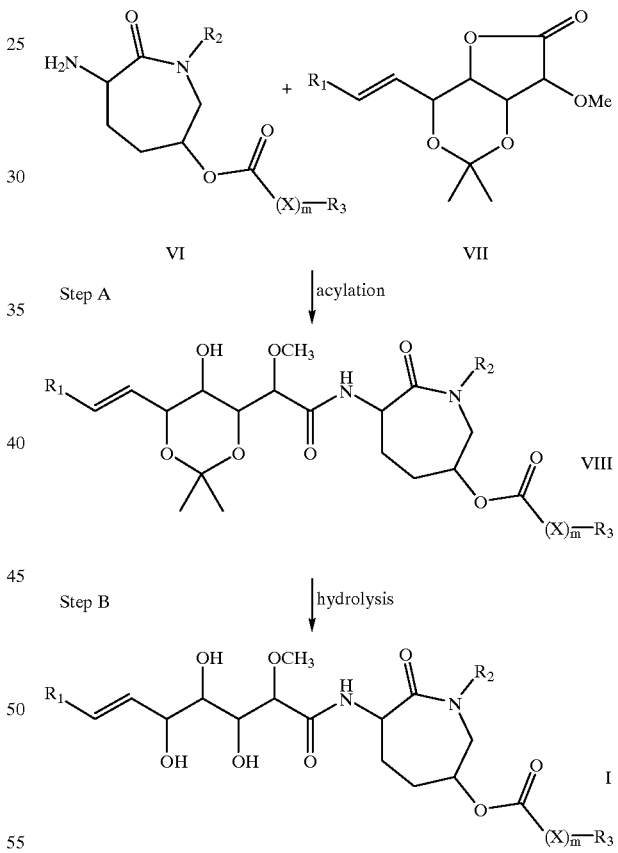

where each $R_1$, $R_2$, X, m and $R_3$ is as defined above.

As to the individual steps, Step A involves the acylation of an aminocaprolactam of formula VI with a lactone compound of formula VII to obtain a diamide compound of formula VIII. The acylation is conducted in a polar, organic solvent, preferably a protic polar solvent such as isopropanol, at a temperature slightly below or at the reflux temperature of the solvent employed for a period of between 4 and 48 hours.

Step B concerns the hydrolysis of the 1,3-dioxane group common to a diamide compound of formula VIII, to obtain a substituted caprolactam compound of formula I. The hydrolysis is typically carried out by dissolving the diamide in a mixture of solvents consisting of 1) a protic acid, preferably an organic acid such as trifluoroacetic acid, 2) a protic solvent, preferably water, and 3) an inert organic solvent, preferably a cyclic ether such as tetrahydrofuran, at a temperature of between 0° C. and 25° C. for a period of between 5 minutes and 2 hours. Alternatively, the diamide compounds of formula VIII may be prepared according to the following 3-step reaction scheme:

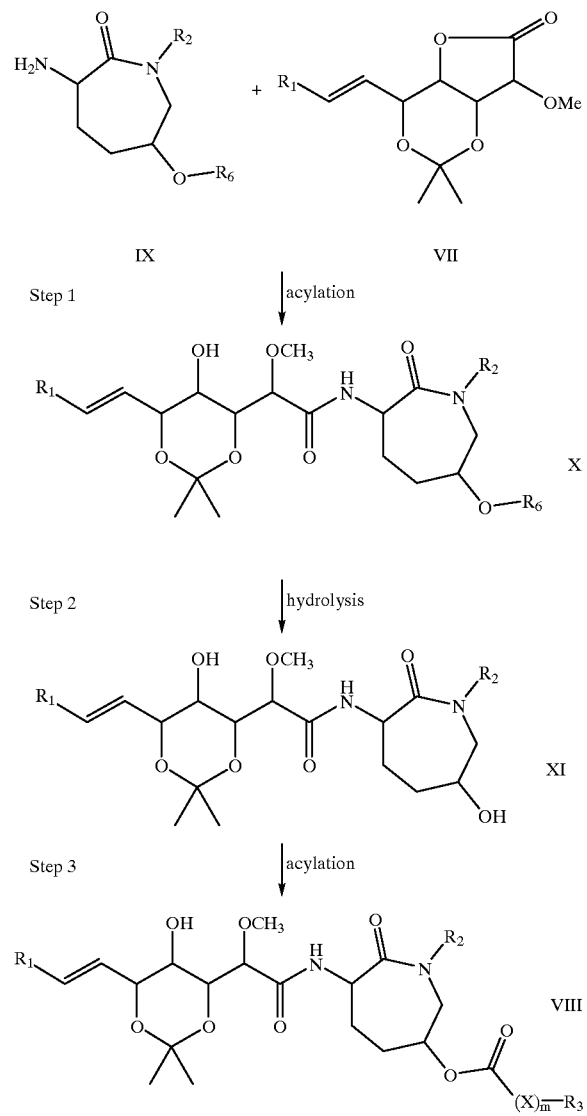

where X, m and $R_3$ and each $R_1$ and $R_2$ are as defined above, and $R_6$ is an alcohol protective group. Preferably, $R_6$ is a silyl group such as tert-butyldimethylsilyl.

As to the individual steps, Step 1 involves the acylation of an aminocaprolactam of formula IX with a lactone compound of formula VII to obtain a diamide compound of formula X. The acylation is conducted in the presence of a base, preferably an alkylamine base such as diisopropylethylamine, and a polar, organic solvent, preferably a protic polar solvent such as isopropanol, at a temperature slightly below or at the reflux temperature of the solvent employed for a period of between 4 and 48 hours.

Step 2 concerns the hydrolysis of the group $R_6$ common to a diamide compound of formula X to obtain a hydroxycaprolactam compound of formula XI. The hydrolysis is typically carried out in the presence of fluoride, preferably a fluoride salt such as tetrabutyl-ammonium fluoride, and an inert organic solvent, preferably a cyclic ether such as tetrahydrofuran, at a temperature of between 0° C. and 25° C. for a period of between 5 minutes and 2 hours.

Step 3 concerns the acylation of a hydroxycaprolactam compound of formula XI by reacting it with an acid chloride of formula $R_3(X)_m COCl$ where $R_3$, X and m are as defined above, to obtain a diamide compound of formula VIII. The acylation is conducted in the presence of a base, preferably an alkylamine base such as triethylamine, and an inert organic solvent, preferably a chlorinated alkane such as dichloromethane, at a temperature of between −78° C. and 25° C. for a period of between 1 and 24 hours.

Alternatively, the acylation of a hydroxycaprolactam compound of formula XI in Step 3 may be carried out with a carboxylic acid of formula $R_3(X)_m CO_2H$ where $R_3$, X and m are as defined above, in the presence of a carboxylic acid coupling reagent, preferably a diimide such as 1-(3-dimethylaminopropyl)-3-ethylcarbodiimide hydrochloride, and a suitable activating agent common to diimide coupling reactions, preferably a substituted pyridine such a 4-dimethylaminopyridine, and an inert organic solvent, preferably a chlorinated alkane such as dichloromethane, at a temperature of between −78° C. and 25° C. for a period of between 1 and 24 hours.

The aminocaprolactam compounds of formula VI may be prepared as depicted below:

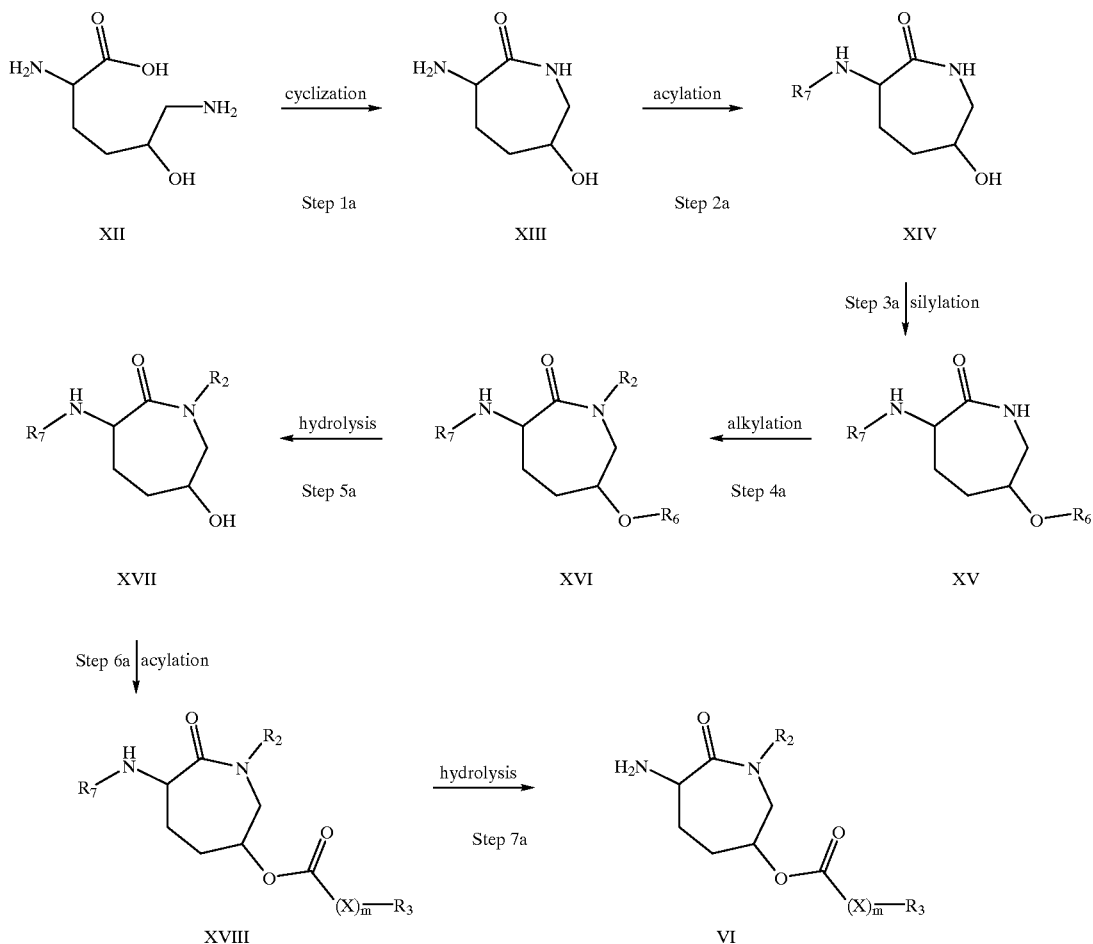

where each $R_6$, $R_2$, X, m and $R_3$ is as defined above, and each $R_7$ is a carbonyl-containing group. Preferably, $R_7$ is alkoxycarbonyl such as t-butyloxycarbonyl.

As to the individual steps, Step 1a involves the cyclization of hydroxylysine (or any salt or hydrate preparation thereof) XII to obtain hydroxycyclolysine XIII. The cyclization is typically carried out in the presence of a coupling reagent, preferably a diimide such as 1-(3-dimethylaminopropyl)-3-ethylcarbodiimide hydrochloride, and a suitable activating agent common to diimide coupling reactions, preferably an N-hydroxy compound such as 1-hydroxybenztriazole hydrate, and a base, preferably an alkylamine base such as triethylamine, and a polar organic solvent, preferably an amide such as N,N-dimethylformamide, at a temperature of between 0° C. and 40° C. for a period of between 12 and 72 hours.

Step 2a involves the N-acylation of hydroxycyclolysine XIII to obtain an N-acylhydroxycyclolysine compound of formula XIV. The acylating agent is typically an acid chloride or an anhydride. When $R_7$ is t-butyloxycarbonyl, the acylating agent is di-tert-butyldicarbonate. The reaction is carried out in the presence of a base, preferably an alkylamine base such as triethylamine, and a polar organic solvent, preferably an amide such as N,N-dimethylformamide, at a temperature of between 0° C. and 40° C. for a period of between 1 and 24 hours.

Step 3a involves the O-silylation of an N-acylhydroxycyclolysine compound of formula XIV to obtain a silyl ether compound of formula XV. The silylating agent is typically a silyl chloride or trifluoromethanesulfonate. When $R_6$ is tert-butyldimethylsilyl, the silylating agent is tert-butyldimethylsilylchloride. The reaction is carried out in the presence of a base, preferably a mild base such as imidazole, and a polar organic solvent, preferably an amide such as N,N-dimethylformamide, at a temperature of between 0° C. and 40° C. for a period of between 1 and 24 hours.

Step 4a involves the N-alkylation of a silyl ether compound of formula XV with an alkyl (defined as $R_2$ above) halide or sulfonate to obtain an N-alkyl caprolactam compound of formula XVI. The alkylation is conducted in the presence of a strong base, preferably an alkali metal amide such as sodium bis(trimethylsilyl)amide, and an inert organic solvent, preferably a cyclic ether such as tetrahydrofuran, at a temperature of between −100° C. and 25° C. for a period of between 5 minutes and 2 hours.

Step 5a concerns the hydrolysis of the group $R_6$ common to an N-alkyl caprolactam compound of formula XVI, to obtain a hydroxycaprolactam compound of formula XVII. The hydrolysis is typically carried out in the presence of fluoride, preferably a fluoride salt such as tetrabutylammonium fluoride, and an inert organic solvent, preferably a cyclic ether such as tetrahydrofuran, at a temperature of between 0° C. and 25° C. for a period of between 5 minutes and 2 hours.

Step 6a concerns the acylation of a hydroxycaprolactam compound of formula XVII to obtain an ester compound of formula XVIII by reacting it with an acid chloride of formula $R_3(X)_m COCl$ where $R_3$, X and m are as defined above, in the presence of a base, preferably an alkylamine base such as triethylamine, and an inert organic solvent, preferably a chlorinated alkane such as dichloromethane, at a temperature of between −78° C. and 25° C. for a period of between 1 and 24 hours.

Alternatively, the acylation of a hydroxycaprolactam compound of formula XVII in Step 6a may be carried out with a carboxylic acid of formula $R_3(X)_m CO_2H$ where $R_3$, X and m are as defined above, in the presence of a carboxylic acid coupling reagent, preferably a diimide such as 1-(3-dimethylaminopropyl)-3-ethylcarbodiimide hydrochloride, and a suitable activating agent common to diimide coupling reactions, preferably a substituted pyridine such a 4-dimethylaminopyridine, and an inert organic solvent, preferably a chlorinated alkane such as dichloromethane, at a temperature of between −78° C. and 25° C. for a period of between 1 and 24 hours.

Step 7a concerns the hydrolysis of the group $R_7$ on an ester compound of formula XVIII to obtain an aminocaprolactam compound of formula VI. The hydrolysis is typically carried out in the presence of a protic acid, preferably an organic acid such as trifluoroacetic acid, hydrogen or a silyl halide, preferably a silyl iodide such as trimethylsilyl iodide, and an inert organic solvent, preferably a chlorinated alkane such as dichloromethane, at a temperature of between −100° C. and 25° C. for a period of between 1 minute and 2 hours.

The aminocaprolactam compounds of formula VIa may be prepared as depicted below:

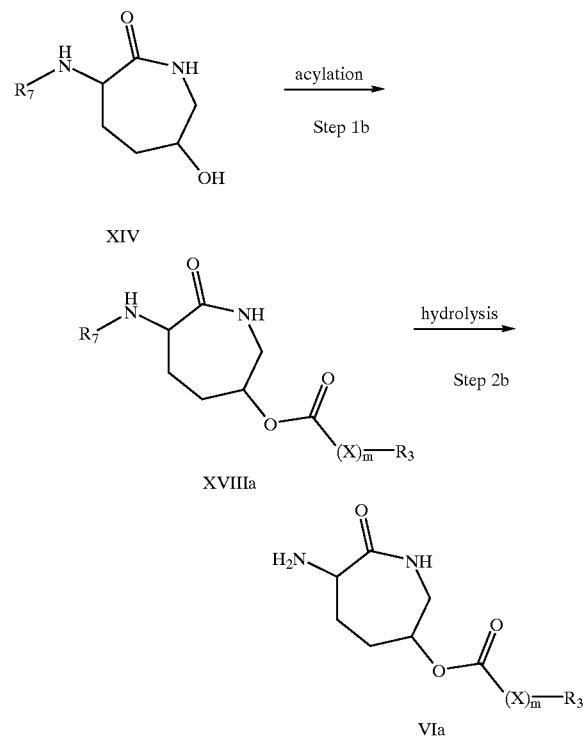

where each $R_7$, X, m, and $R_3$ is as defined above.

As to the individual steps, Step 1b concerns the acylation of a hydroxycaprolactam compound of formula XIV to obtain an ester compound of formula XVIIIa by reacting it with an acid chloride of formula $R_3(X)_m COCl$ where $R_3$, X and m are as defined above, in the presence of a base, preferably an alkylamine base such as triethylamine, and an inert organic solvent, preferably a chlorinated alkane such as dichloromethane, at a temperature of between −78° C. and 25° C. for a period of between 1 and 24 hours.

Alternatively, the acylation of a hydroxycaprolactam compound of formula XIV in Step 1b may be carried out with a carboxylic acid of formula $R_3(X)_m CO_2H$ where $R_3$, X and m are as defined above, in the presence of a carboxylic acid coupling reagent, preferably a diimide such as 1-(3-dimethylaminopropyl)-3-ethylcarbodiimide hydrochloride, and a suitable activating agent common to diimide coupling reactions, preferably a substituted pyridine such a 4-dimethylaminopyridine, and an inert organic solvent, preferably a chlorinated alkane such as dichloromethane, at a temperature of between −78° C. and 25° C. for a period of between 1 and 24 hours.

Step 2b concerns the hydrolysis of the group $R_7$ on an ester compound of formula XVIIIa to obtain an aminocaprolactam compound of formula VIa. The hydrolysis is typically carried out in the presence of an protic acid, preferably an organic acid such as trifluoroacetic acid, hydrogen or a silyl halide, preferably a silyl iodide such as trimethylsilyl iodide, and an inert organic solvent, preferably a chlorinated alkane such as dichloromethane, at a temperature of between −100° C. and 25° C. for a period of between 1 minute and 12 hours.

The aminocaprolactam compounds of formula IXa may be prepared as depicted below:

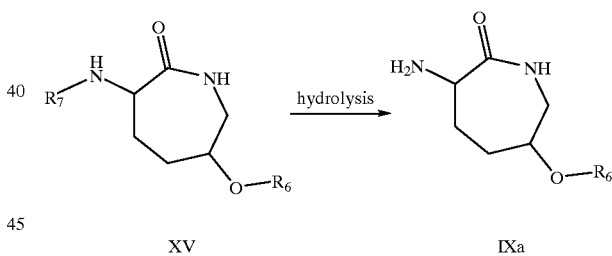

where $R_7$ and each $R_6$ are as defined above. The reaction concerns the hydrolysis of the group $R_7$ on an ester compound of formula XV to obtain an aminocaprolactam compound of formula IXa. The hydrolysis is typically carried out in the presence of a protic acid, preferably an organic acid such as trifluoroacetic acid, hydrogen or a silyl halide, preferably a silyl iodide such as trimethylsilyl iodide, and an inert organic solvent, preferably a chlorinated alkane such as dichloromethane, at a temperature of between −100° C. and 25° C. for a period of between 1 minute and 2 hours.

The lactone compounds of formula VII may be prepared as depicted below:

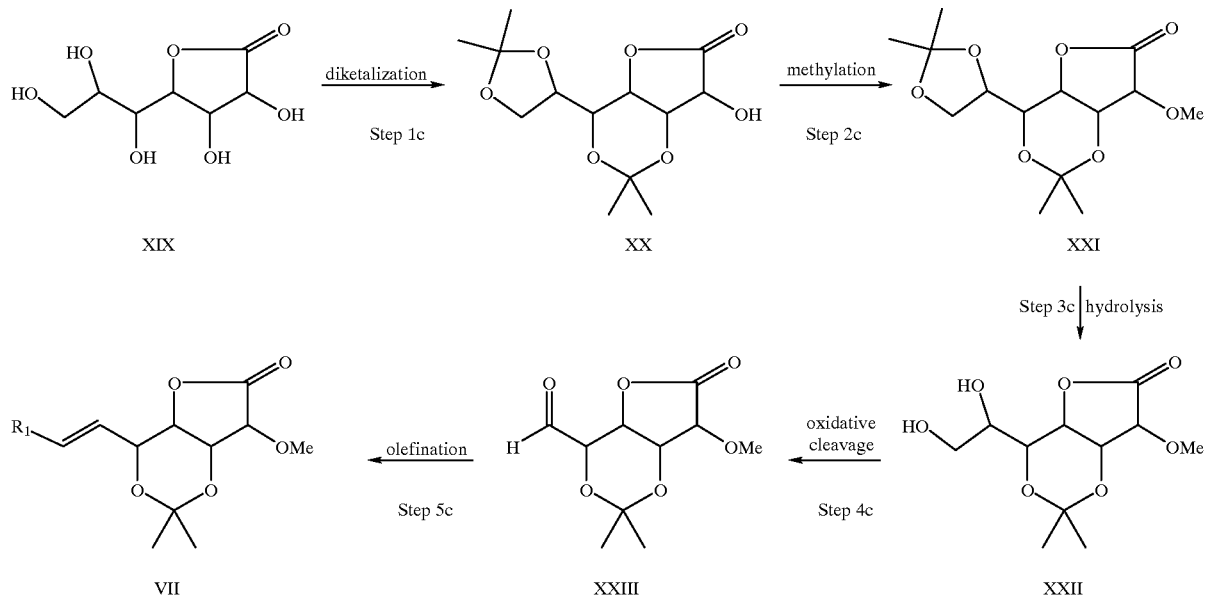

where $R_1$ is as defined above.

As to the individual steps, Step 1c involves the diketalization of polyhydroxylated lactone of formula XIX with acetone to obtain bis(acetonide) XX. The diketalization is conducted in acetone as solvent using a catalyst such as iodine at a temperature of between 0 ° C. and the reflux temperature for a period of between 2 and 48 hours.

Step 2c involves the methylation of bis(acetonide) XX with a methylating agent such as methyl iodide to obtain the methyl ether XXI. The methylation is conducted in the presence of water and a base, preferably a metal oxide such as silver oxide, and an inert organic solvent, preferably a chlorinated alkane such as dichloromethane, at a temperature of between 0° C. and the reflux temperature for a period of between 12 hours and 7 days.

Step 3c involves the hydrolysis of methyl ether XXI to obtain the dihydroxy compound of formula XXII. The hydrolysis is conducted in the presence of water and a protic acid, preferably a carboxylic acid such as acetic acid, at a temperature of between 5° C. and 35° C. for a period of between 1 and 24 hours.

Step 4c involves the oxidative cleavage of dihydroxy compound XXII to obtain the aldehyde XXIII. The reaction is conducted in the presence of an oxidant, preferably a periodate salt such as sodium periodate, in a protic solvent, preferably an alkanol such as methanol, at a temperature of between 0° C. and 25° C. for a period of between 10 minutes and 4 hours.

Step 5c involves the olefination of aldehyde XXIII to obtain a lactone compound of formula VII. The olefination is conducted in the presence of an organometallic compound, preferably an organochromium compound such as the transient species generated from chromium(II) chloride and a diiodoalkane (defined as $R_1CHI_2$ where $R_1$ is as defined above), in the presence of a solvent mixture consisting of 1) a polar organic solvent, preferably an amide such as N,N-dimethylformamide, and 2) an inert organic solvent, preferably a cyclic ether such as tetrahydrofuran, at a temperature of between –80° C. and 25 ° C. for a period of between 5 minutes and 4 hours.

Although the product of each reaction described above may, if desired, be purified by conventional techniques such as chromatography or recrystallization (if a solid), the crude product of one reaction is advantageously employed in the following reaction without purification.

As is evident to those skilled in the art, the substituted caprolactam compounds of formula I contain asymmetric carbon atoms. It should be understood, therefore, that the individual stereoisomers are contemplated as being included within the scope of this invention.

As indicated above, certain of the compounds of formula I form pharmaceutically acceptable acid addition salts. For example, the free base of a compound of formula I can be reacted with hydrochloric acid to form the corresponding hydrochloride salt form, whereas reacting the free base of the compound of formula I with methanesulfonic acid forms the corresponding mesylate salt form. All pharmaceutically acceptable addition salt forms of the compounds of formula I are intended to be embraced by the scope of this invention.

In a further embodiment, the present invention relates to a process for preparing a caprolactam compound of formula I which comprises, in a first step, acylating an amino caprolactam compound of formula VI

VI

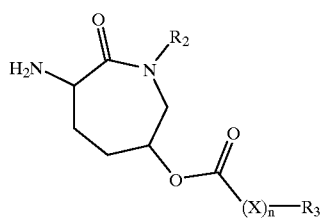

with a lactone compound of formula VII

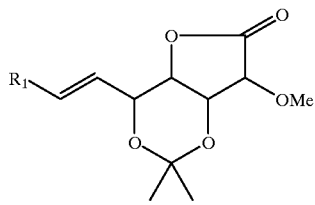

VII in the presence of a polar, organic solvent to obtain a diamide compound of formula VIII

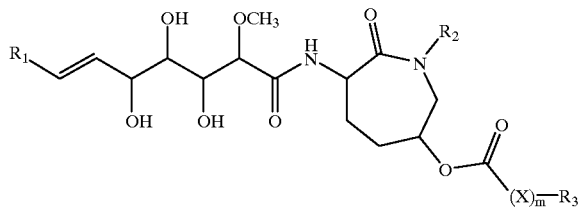

VIII where each of $R_1$, $R_2$, X, m and $R_3$ are as defined above and, in a second step, hydrolyzing the diamide compound obtained in the first step by dissolving it in a mixture of solvents to obtain the desired caprolactam compound of formula I. Preferably, the acylation in the first step is conducted in isopropanol at a temperature slightly below or at the reflux temperature of the isopropanol, whereas the hydrolysis in the second step is conducted in a mixture consisting of a protic, organic acid, a protic solvent and an inert, organic solvent, more preferably a mixture consisting of trifluoroacetic acid, water and tetrahydrofuran.

As indicated above, all of the compounds of formula 1, and their corresponding pharmaceutically acceptable acid addition salts, are anti-tumor agents and are, therefore, useful in inhibiting the growth of various lymphomas, sarcomas, carcinomas, myelomas, and leukemia cell lines. The anti-tumor activity of the compounds of formula I may be demonstrated employing the Anchorage Dependent Growth Monolayer Assay (ADGMA) which measures the growth inhibitory effects of test compounds on proliferation of adherent cell monolayers. This assay was adapted from the 60 cell line assay used by the National Cancer Institute (NCI) with the following modifications: 1) a single cell line representative for the important tumor type, viz., MDA-MB435 breast carcinoma was utilized; 2) a tetrazolium derivative, viz., MTS, was utilized to determine cell density.

The ADGMA compares the number of viable cells following a 3-day exposure to a test compound relative to a number of cells present at the time the test compound was added. Cell viability is measured using a tetrazolium derivative, viz., 3-(4,5-dimethylthiazol-2-yl)-5-(3-carboxymethoxyphenyl)-2-(4-sulfophenyl)-2H-tetrazolium, inner salt (MTS) that is metabolically reduced in the presence of an electron coupling agent (PMS; phenazine methosulfate) by viable cells to a water-soluble formazan derivative. The absorbance at 490 nm ($A_{490}$) of the formazan derivative is proportional to the number of viable cells. The $IC_{50}$ for a test compound is the concentration of compound required to reduce the final cell number to 50% of the final control cell number. If cell proliferation is inhibited, the assay further defines compounds as cytostatic (cell number after 3-day compound incubation >cell number at time of compound addition) or cytotoxic (cell number after 3day compound incubation <cell number at time of compound addition).

The MDA-MB-435 breast carcinoma line was obtained from the American Type Culture Collection (ATCC) and used between passages 4–20 following thawing. MDA-MB-435 breast carcinoma was maintained and plated in DME/F12 medium containing 10% fetal bovine serum, 15 mM HEPES (pH=7.4), penicillin 100 units/mL, and streptomycin 100 μg/mL.

Cell lines are trypsinized and counted using a Coulter counter to determine plating densities. Cells are then plated in their respective maintenance media (100 μL/well) in 96 well plates at the following densities: MDA-MB-435, 3,000 cells/well. The number of cells plates as determined in preliminary experiments, results in cell densities of 75–90% of confluency by 4 days after plating. Initial cell densities, assayed one day after plating, are roughly 0.15–0.20 absorbance units greater than the media blank. Ninety-six well plates are seeded on day 0 and the test compounds are added on day 1. A control plate is created for each cell line that receives media only in row A and cells in row B. One day following plating, test compounds are added (in a final volume of 100 μL) to the test plates. Control plates receive 10 μL MTS mixture (prepared fresh on day of addition to cell plates at a ratio of 10 μL of a 0.92 mg/mL solution of PMS to a 190 μL of a 2 mg/mL solution of MTS) and 100 μL media. $A_{490}$ of control plates is read 4 h after MTS addition to determine initial cell density values for each cell line. Three days after addition of test compound, 10 μL/well of MTS mixture is added to the test plates and $A_{490}$ is read 4 h later. $A_{490}$ values for wells containing cells are corrected for media absorbance, then normalized to initial density readings to determine percent net growth. $IC_{50}$ values are determined from graphs of percent net growth as a function of compound concentration. Percent net growth is calculated as (Cell+Drug $A_{490}$–Initial $A_{490}$/Cell+Drug Vehicle $A_{490}$–Initial $A_{490}$).

The following $IC_{50}$ values (average±S.D.) in μM were obtained:

TABLE 1

| Compound | MDA-MB-435 |
|---|---|
| Ex. 1 | 0.068 ± 0.04 |
| Ex. 2 | 0.115 ± 0.04 |
| Ex. 3 | 0.032 ± 0.014 |
| Ex. 4 | 0.01 ± 0.01 |
| Ex. 5 | 0.465 ± 0.204 |
| Ex. 6 | 0.065 ± 0.001 |
| Ex. 7 | 0.262 ± 0.07 |
| Ex. 8 | 0.175 ± 0.007 |
| Ex. 9 | 0.335 ± 0.141 |
| Ex. 10 | 0.008 ± 0.004 |
| Ex. 11 | 0.019 ± 0.005 |
| Ex. 12 | 0.034 ± 0.046 |
| Ex. 13 | 0.30 ± 0.00 |
| Ex. 14 | 1.24 ± 0.20 |
| doxorubicin (a known antineoplastic compound) | 0.137 ± 0.105 |

The anti-tumor activity of the compounds of formula I may further be demonstrated employing the athymic (T cell deficient) nude mouse model which has been and remains the standard for drug discovery and development in preclinical oncology. Utilizing this model, one can measure the ability of test compounds to inhibit the growth of human tumor xenografts growing subcutaneously (s.c.) in athymic nude mice. The histologic tumor type employed was MDA-MB435 breast carcinoma.

Briefly, 3 million cells were implanted s.c. into the right flank of athymic (nu/nu) mice, and were allowed to grow until a mass of approximately 30 mm³ was established. The test compounds are administered three times per week intravenously (i.v.) for three weeks in 5% dextrose, 10% DMSO in water. The test compounds are administered in dose-response fashion in order to evaluate and document the full potential range of activity (efficacy and toxicity) for a given compound. Positive controls are carried out with doxorubicin administered 3 times per week i.v.

Toxicity was monitored by recording average group body weights twice weekly, and by daily observation of general health. Efficacy was monitored by taking measurements of tumor length, width, and depth weekly using digital calipers coupled to automated data collectors. Mean tumor volume (MTV) at initiation of therapy was subtracted from final MTV in order to express the actual tumor growth during treatment (Δ MTV). Anti-tumor activity was expressed as % T/C (ΔMTV of treated group ÷ΔMTV of control group X100). Statistical significance was evaluated using a one-tailed Student's t-test (p<0.05).

The following results were obtained for compounds Ex. 1–Ex.10 tested against MDA-MB-435 tumor xenografts 3×/week for 3 weeks:

TABLE 2

| Compound | Dose (μmol/kg) | Δ MTV (mm³) | % T/C | Dead/Total |
|---|---|---|---|---|
| Ex. 1 | 10 | 107 | 61* | 0/8 |
| Ex. 1 | 33 | 43 | 24* | 0/8 |
| Ex. 1 | 100 | −11 | −6* | 0/8 |
| Ex. 2 | 10 | 94 | 67 | 0/8 |
| Ex. 2 | 33 | 19 | 13* | 0/8 |
| Ex. 3 | 10 | 69 | 39* | 0/8 |
| Ex. 3 | 33 | 49 | 28* | 0/8 |
| Ex. 4 | 10 | 93 | 53* | 0/8 |
| Ex. 4 | 33 | 21 | 12* | 0/8 |
| Ex. 4 | 100 | −23 | −13* | 0/8 |
| Ex. 5 | 10 | 130 | 92 | 0/8 |
| Ex. 5 | 33 | 62 | 44* | 0/8 |
| Ex. 6 | 10 | 66 | 47* | 0/8 |
| Ex. 6 | 33 | 48 | 34* | 0/8 |
| Ex. 7 | 10 | 101 | 72 | 0/8 |
| Ex. 7 | 33 | 61 | 43* | 0/8 |
| Ex. 8 | 10 | 87 | 62 | 0/8 |
| Ex. 8 | 33 | 94 | 67 | 0/8 |
| Ex. 9 | 10 | 107 | 76 | 0/8 |
| Ex. 9 | 33 | 68 | 48* | 0/8 |
| Ex. 10 | 10 | 115 | 64* | 0/8 |
| Ex. 10 | 33 | 4 | 2* | 0/8 |
| Ex. 11 | 10 | 135 | 76 | 0/8 |
| Ex. 11 | 33 | 76 | 43* | 0/8 |
| Ex. 12 | 10 | 78 | 52 | 0/8 |
| Ex. 12 | 33 | 11 | 7* | 0/8 |
| doxorubicin | 2 mg/kg | 74 | 42* | 0/8 |

*% T/C values were statistically significant (p = <0.05; Student's t-test).

The precise dosage of the compounds of formula I to be employed for inhibiting tumors depends upon several factors including the host, the nature and the severity of the condition being treated, the mode of administration and the particular compound employed. However, in general, satisfactory inhibition of tumors is achieved when a compound of formula I is administered parenterally, e.g., intraperitoneally, intravenously, intramuscularly, subcutaneously, intratumorally, or rectally, or enterally, e.g., orally, preferably intravenously or orally, more preferably intravenously at a daily dosage of 1–300 mg/kg body weight or, for most larger primates, a daily dosage of 50–5000, preferably 500–3000 mg. A preferred intravenous daily dosage is 1–75 mg/kg body weight or, for most larger primates, a daily dosage of 50–1500 mg. A typical intravenous dosage is 20 mg/kg, three to five times a week.

Usually, a small dose is administered initially and the dosage is gradually increased until the optimal dosage for the host under treatment is determined. The upper limit of dosage is that imposed by side effects and can be determined by trial for the host being treated.

The compounds of formula I may be combined with one or more pharmaceutically acceptable carriers and, optionally, one or more other conventional pharmaceutical adjuvants and administered enterally, e.g. orally, in the form of tablets, capsules, caplets, etc. or parenterally, e.g., intraperitoneally or intravenously, in the form of sterile injectable solutions or suspensions. The enteral and parenteral compositions may be prepared by conventional means.

The infusion solutions according to the present invention are preferably sterile. This may be readily accomplished, e.g. by filtration through sterile filtration membranes. Aseptic formation of any composition in liquid form, the aseptic filling of vials and/or combining a pharmaceutical composition of the present invention with a suitable diluent under aseptic conditions are well known to the skilled addressee.

The compounds of formula I may be formulated into enteral and parenteral pharmaceutical compositions containing an amount of the active substance that is effective for inhibiting tumors, such compositions in unit dosage form and such compositions comprising a pharmaceutically acceptable carrier.

The following examples show representative compounds encompassed by this invention and their synthesis. However, it should be clearly understood that it is for purposes of illustration only.

EXAMPLE 1

(2R, 3R, 4S, 5R, 6E)-3,4,5-trihydroxy-2-methoxy-8, 8-dimethyl-N-[(3S, 6R)-hexahydro-2-oxo-6-(cyclohexylcarbonyl)oxy-2H-azepin-3-yl]non-6-enamide a) Preparation of 3,5:6,7-bis-O-(1-methylethylidene)-α-D-glucoheptonic γ-lactone.

α-D-Glucoheptonic γ-lactone (500 g, 2.4 mol) is added into 9 L of acetone in a 5 gal plastic drum. The mixture is agitated mechanically until most of the solid dissolved (15–20 min). Iodine (60 g, 0.236 mol) is added portionwise into the lactone soln over 5–10 min. The resulting mixture is stirred overnight. A saturated soln of $Na_2S_2O_3$ (1.3 L) is added to the iodine soln to quench the reaction. The resulting soln is concd to about half of its original volume in vacuo, and brine soln (5 L) is added. The resulting mixture is extracted with 3×1.2 L EtOAc. All organic layers are combined and evaporated to dryness. The solid is slurried with a mixture of ether and hexane (3:7), and filtered. The filter cake is washed with $Et_2O$ (50 mL) and air dried, giving 599 g of the desired compound as a white powder (86.5%): ¹H NMR ($CDCl_3$) δ 4.62 (m, 1H), 4.50 (m, 1H), 4.35 (m, 2H), 4.07 (m, 1H), 3.93 (m, 1H), 3.82 (dd, 1H), 3.08 (d, 1H), 1.51 (s, 3H), 1.44 (s, 3H), 1.39 (s, 3H), 1.35 (s, 3H); ¹³C NMR ($CDCl_3$) δ 174.4, 109.4, 98.6, 72.8, 71.4, 69.3, 68.4, 67.8, 66.7, 28.6, 26.7, 24.6, 19.3.

b) Preparation of 2-O-methyl-3,5:6,7-bis-O-(1-methylethylidene)-α-D-glucoheptonic γ-lactone.

3,5:6,7-bis-O-(1-methylethylidene)-α-D-glucoheptonic γ-lactone (719 g, 2.49 mol) is added into 4.5 L of $CH_2Cl_2$ in a 5 gal plastic drum. The mixture is stirred under $N_2$. Iodomethane (2500 g, 17.6 mol) is added immediately followed by addition of silver(I)oxide (1750 g, 7.58 mol). Water (30 mL) is added to the reaction mixture. Ice bath is used to maintain the reaction temp at 15–30° C. The reaction is stirred in the absence of light for 18 h. After diluting the reaction mixture with 1.5 L of $CH_2Cl_2$, the solid is filtered and washed with an additional 2.2 L of $CH_2Cl_2$. The undesired solid is discarded and the filtrate is evaporated to dryness. The residue is slurried in $Et_2O$ (1.5 L), filtered, and dried to give 618 g product (82%): $^1H$ NMR ($CDCl_3$) δ 4.75 (m, 1H), 4.33 (m, 1H), 4.29 (m, 1H), 4.15 (m, 1H), 4.07 (m, 1H), 3.96 (dd, 1H), 3.83 (dd, 1H), 3.65 (s, 3H), 1.57 (s, 3H), 1.42 (s, 6H), 1.35 (s, 3H); $^{13}C$ NMR ($CDCl_3$) δ 172.5, 109.6, 98.5, 79.0, 73.1, 69.5, 68.6, 67.5, 66.9, 59.1, 28.9, 26.9, 24.9, 19.4.

c) Preparation of 2-O-Methyl-3,5-O-(1-methylethylidene)-α-D-glucoheptonic γ-lactone.

2-O-methyl-3,5:6,7-bis-O-(1-methylethylidene)-α-D-glucoheptonic γ-lactone (618 g, 2.05 mol) is dissolved in 8 L of a mixture of acetic acid and water (1:1) over 30 min. The soln is stirred at ambient temp overnight. The soln is evaporated to dryness in vacuo. The solid is slurried in 3–5 L of hot acetone and filtered. After oven drying at 20–30° C., 363 g of the desired compound is obtained (67.6 %). $^1H$ NMR($CDCl_3$): δ 4.92 (d, 1H), 4.80 (m, 1H), 4.47 (d, 1H), 4.42 (t, 1H), 4.39 (m, 1H), 3.95 (dd, 1H), 3.75 (m, 2H), 3.4 (s, 3H), 2.5 (m, 1H), 1.42 (s, 3H), 1.22 (s, 3H).

d) Preparation of 2,4-O-(1-methylethylidene)-5-O-methyl-L-glucuronic γ-lactone.

2-O-Methyl-3,5-O-(1-methylethylidene)-α-D-glucoheptonic γ-lactone (200 g, 0.76 mol) is dissolved into a 1:1 mixture of methanol and water (3.6 L). The stirred mixture is cooled in an ice water bath to about 8° C. Solid $NaIO_4$ (213 g, 0.98 mol) is added portionwise. Reaction is complete within 40 min as indicated by TLC (silica gel, 5% methanol, 15% EtOAc in $CH_2Cl_2$). Solid NaCl is added into the reaction mixture to saturate the methanolic soln. The solid is filtered and washed with 2 L $CH_2Cl_2$. The filtrate is extracted with 7×500 mL $CH_2Cl_2$. Combined organic layers are dried over $Na_2SO_4$, filtered and concd to a syrup, which formed a precipitate upon addition of hexane. The solid is filtered and rinsed with $Et_2O$. A portion of the crude product (50 g) is dissolved in 3 L $CHCl_3$ and heated to reflux. After rotary evaporation of 2.1 L of $CHCl_3$ at atmospheric pressure (methanol is driven out of the system by coevaporation with $CHCl_3$) the residue is evaporated to dryness. 44 g of the desired product is obtained as a solid after drying in vacuo overnight. $^1H$ NMR (CDCl3): δ 9.60 (s, 1H), 4.78 (m, 1H), 4.42 (s, 2H), 4.15 (dd, 1H), 3.65 (s, 3H), 1.58 (s, 3H), 1.55 (s, 3H); $^{13}C$ NMR ($CDCl_3$) δ 198.8, 171.9, 99.0, 78.4, 74.4, 72.9, 68.4, 67.4, 59.2, 28.7, 19.0.

e) Preparation of (6E)-6,7,8,9-tetradeoxy-8,8-dimethyl-2-O-methyl-3,5-O-(1-methylethylidene)-gulo-non-6-enonic acid lactone.

Into a 2 L round bottom flask, is added $CrCl_2$ (50 g, 41 mmol ), anhydrous THF (750 mL), and DMF (32 mL). The mixture is stirred under $N_2$ for 1 h. A soln of 2,4-O-(1-methylethylidene)-5-O-methyl-L-glucuronic γ-lactone (12 g, 50 mmol), 1,1-diiodo-2,2-dimethylpropane (15 mL), and 500 mL of anhydrous THF is added slowly into the reaction mixture. After the addition, the reaction mixture is stirred at ambient temp for 1.5 h. The reaction is quenched with satd. aq. $NH_4Cl$. The residue is partitioned with EtOAc/water and chromatographed (5% EtOAc-$CH_2Cl_2$) to give 9 g (63%) of the desired compound as a white crystalline solid: $^1HNMR$ ($CDCl_3$) δ 5.82 (d, 1H), 5.58 (q, 1H), 4.71 (m, 1H), 4.46 (m, 1H), 4.10 (dd, 1H), 4.0 (m, 1H), 3.66 (s, 3H), 1.58 (s, 3H), 1.53 (s, 3H), 1.07 (s, 9 H); $^{13}C$ NMR ($CDCl_3$) δ 172.5, 147.0, 120.2, 98.7, 79.1, 71.9, 70.3, 67.6, 59.2, 33.2, 29.3, 19.3.

f) Preparation of (3S, 6R)-3-(tert-butoxycarbonyl) aminohexahydro-6-hydroxy-2H-azepin-2-one In a 1 l flask (5R)-5-hydroxy-L-lysine (10 g, 0.040 mol), 1-hydroxybenzotriazole hydrate (8.2 g, 0.060 mol) and 1-[3-(dimethylamino)propyl]-3-ethylcarbodiimide-HCl (11.6 g, 0.060 mol) are added to 500 ml DMF with stirring. After 0.5 h triethylamine (16.8 ml, 0.120 mol) is added. The reaction is stirred at rt for 48 h. Di-tert-butyl dicarbonate (17.6 g, 0.080 mol) and triethylamine (16.8 ml, 0.120 mol) are added. Stirring is continued for 16 h. The reaction mixture is filtered to remove triethylamine-HCl and the solvent is removed by rotary evaporation under high vacuum to give a thick oil. The oil is dissolved in 150 ml $CH_2Cl_2$ and applied to a silica gel column (150 g, 40×250 mm). The column is eluted with 3% methanol in $CH_2Cl_2$ to give the crude product as a solid. The crude solid is dissolved in 120 ml hot $CH_2Cl_2$ and cooled to −20 ° C. for 1 h. The resulting solid is filtered and washed with 50 ml $CH_2Cl_2$. The combined filtrates are evaporated to dryness. $CH_2Cl_2$ (40 ml) is added to this residue and the resulting slurry is stirred for 0.5 h at rt. The slurry is filtered and the solid washed with 25 ml $CH_2Cl_2$. The solids are combined to give 5.57 g of (3S, 6R)-3-(tert-butoxycarbonyl) aminohexahydro-6-hydroxy-2H-azepin-2-one. 300 MHz $^1H$ NMR (DMSO) δ 7.42 (1H, t, J=5.1 Hz), 6.38 (1H, d, J=6.6 Hz), 4.60 (1H, d, J=4.2 Hz), 4.07 (1H, m), 3.74 (1H, m), 3.32 (1H, m), 3.03 (1H, m), 1.8–1.5 (4H, m), 1.39 (9H, s).

g) Preparation of (3S, 6R)-3-(tert-butoxycarbonyl) aminohexahydro-6-(cyclohexanecarbonyl) oxy-2H-azepin-2-one.

Triethylamine (8.4 mL, 60 mmol) is added to a solution of cyclohexanecarbonyl chloride (6.3 g, 43.0 mmol), (3S, 6R)-3-(tert-butoxycarbonyl)aminohexahydro-6-hydroxy-2H-azepin-2-one (7.0 g, 28.7 mmol) and 100 mL of $CH_2Cl_2$ at 5° C. The reaction mixture is stirred at room temp. overnight. The reaction mixture is then partitioned with water, and the organic layer is dried ($Na_2SO_4$), and concentrated with rotary evaporation. The resulting residue is chromatographed (5% EtOAc—$CH_2Cl_2$) to give 10.1 (99.5% of (3S, 6R)-3-(tert-butoxycarbonyl) aminohexahydro-6-(cycohexanecarbonyl)oxy-2H-azepin-2-one as a white solid: $^1H$ NMR ($CDCl_3$): δ 5.89 (d, J=5.27Hz, 1H), 5.65 (t, J=4.90 Hz, 1H), 4.89 (s, 1H), 4.30 (q, J=4.14Hz, 1H), 3.49 (m, 2H), 2.31 (tt, J=10.92Hz and 3.39 Hz, 1H), 2.13 (d, J=14.32 Hz, 1H), 1.98 (d, J=13.56Hz, 2H), 1.88 (d, J=14.31Hz, 2H), 1.75 (d, J=11.3 Hz, 2H), 1.66 (s, 2H), 1.45 (s, 9H), 1.30 (m, 5H).

h) Preparation of (3S, 6R)-3-aminohexahydro-6-(cyclohexanecarbonyl)oxy-2H-azepin-2-one.

To a solution of (3S, 6R)-3-(tert-butoxycarbonyl) aminohexahydro-6-(cyclohexanecarbonyl) oxy-2H-azepin-2-one (10 g, 28.2 mmol) in 40 mL of $CH_2Cl_2$ is added TFA (25 mL) at room temp., and the reaction solution is stirred at room temp. for 1 hr, then concd via rotary evaporation (bath temp<20° C.). The residue is diluted with $CH_2Cl_2$ (100 mL), and washed with $NH_4OH$ (10 mL) and then water (2×20 mL) and dried ($Na_2SO_4$). The reaction mixture is adsorbed on silica and chromatographed (5% methanol-$CH_2Cl_2$) to give 6.0 (85.0%) of (3S, 6R)-3-aminohexahydro-6-(cyclohexanecarbonyl)oxy-2H-azepin-2-one as a white solid: $^1H$ NMR ($CDCl_3$): δ 6.91 (s, 1H), 4.91 (s, 1H), 4.39 (s, 2H), 3.87 (d, J=9.8 Hz, 1H), 3.48 (t, J=6.02 Hz, 1H), 3.43 (dd, J=15.45Hz and 4.90 Hz, 1H), 2.30 (tt, J=10.92 Hz and 3.39 Hz, 1H), 2.13 (m, 1H), 1.91 (m, 4H), 1.73 (m, 2H), 1.65 (m, 1H), 1.40 (q, J=11.68 Hz, 4H), 1.24 (m, 2H).

i) Preparation of (2R, 3R, 4S, 5R, 6E)-3,5-(methylethylidene)-3,4,5-trihydroxy-2-methoxy-8,8- dimethyl-N-[(3S, 6R)- hexahydro-2-oxo-6-(cyclohexylcarbonyl)oxy-2H-azepin-3-yl]non-6-enamide.

A soln consisting of (6E)-6,7,8,9-tetradeoxy-8,8-dimethyl-2-O-methyl-3,5-O-(1-methyl-ethylidene)-gulo-non-6-enonic acid lactone (1.0 g, 3.5 mmol), (3S, 6R)-3-aminohexahydro-6-cyclohexanecarboxy-2H-azepin-2-one (2.5 g, 9.8 mmol), and i-PrOH (4 mL) is stirred at reflux for 24 h. The reaction mixture is adsorbed on silica and chromatographed (2% methanol-$CH_2Cl_2$) to give 1.85 g (97%) of the desired compound as a white solid: $^1$H NMR ($CDCl_3$) δ 7.58 (d, J=6.341 Hz, 1 H), 5.80 (t, J=7.68 Hz, 1H), 5.78 (d, J=15.83 Hz, 1H), 5.53 (dd, J=15.83 Hz and 6.78 Hz 1H), 4.92 (sd, J=3.39 Hz, 1H), 4.60 (dd, J=0.42 Hz and 7.4 Hz, 1H), 4.28 (d, J=6.79 Hz, 1H), 4.07 (dd, J=7.54 Hz and 1.13 Hz, 1H), 3.90 (d, J=7.15 Hz, 1H), 3.52 (dd, J=12.05 Hz and 7.91 Hz, 2H), 3.48 (s, 3H), 2.82 (d, J=9.04 Hz, 1H), 2.32 (m, 1H), 2.12(m,1H), 2.00 (m, 2H), 1.89 (d, J=13.06 Hz, 2H), 1.75 (m, 4H), 1.66 (m, 1H), 1.46 (d, J=4.90Hz, 6H),1.38 (m, 2H), 1.26 (m, 3H), 1.03 (s. 9H).

j) Preparation of the title compound.

(2R, 3R, 4S, 5R, 6E)-3,5-(methylethylidene)-3,4,5-trihydroxy-2-methoxy-8,8-dimethyl-N-[(3S, 6R)-hexahydro-2-oxo-6-(cyclohexylcarbonyl)oxy-2H-azepin-3-yl]non-6-enamide (3.8 g, 7.1 mmol) is added in one portion to a stirred soln of TFA (10 mL), THF (10 mL), and water (5 mL) at 0° C. The reaction is stirred at this temp for 30 min, concd via rotary evaporation (bath temp <20° C.), mixed with saturated $NH_4HCO_3$ (5 mL), and stirred for 15 min. The mixture is concd in vacuo and chromatographed (2% methanol-$CH_2Cl_2$) to give a white solid with $H_2O$ solubility of 3.7 mg/mL. This material is further purified using preparative hplc (reverse phase eluted with 90% $CH_3CN$-water) to give 2.9 g (82.4%) of the title compound as a white solid, mp 79–80° C.; $^1$H NMR ($CDCl_3$) δ 8.00 (d, J=6.3 Hz, 1H), 5.98 (t, J=5.52 Hz, 1H), 5.83 (d, J=15.77 Hz, 1H), 5.42 (dd, J=15.76 Hz and 7.25 Hz 1H), 4.93 (m, 1H), 5.56 (m, 1H), 4.22 (m, 2H), 3.82 (m, 2H), 3.81 (t, J=5.99 Hz, 1H), 3.55 (s,3H), 3.49 (dd, J=15.77 Hz and 5.36 Hz, 1H), 3.30 (d, J=7.25 Hz, 1H), 3.10 (s, 1H), 2.31 (m, 1H), 2.16 (d, J=11.19 Hz, 1H), 2.00 (m,2H), 1.88 (m, 3H), 1.76 (s, 2H), 1.65 (d, J=0.87 Hz, 1H), 1.42 (m, 2H), 1.25 (m, 4H), 1.02 (s. 9H); $^{13}$C NMR ($CDCl_3$) δ 175.19, 174.11, 172.12, 145.74, 123.20, 81.10, 74.50, 72.75, 72.45, 66.74, 59.93, 51.66, 43.31, 43.22, 33.03, 31.96, 29.43, 29.07, 29.00, 25.70, 25.65, 25.39, 25.36.

EXAMPLE 2

(2R, 3R, 4S, 5R, 6E)-3,4,5-trihydroxy-2-methoxy-8,8-dimethyl-N-[(3S, 6R)-hexahydro-2-oxo-6-(cyclopentylcarbonyl)oxy-2H-azepin-3-yl]non-6-enamide.

Following essentially the procedure of Example 1g) and using in place of cyclohexane-carbonyl chloride, an approximately equivalent amount of cyclopentanecarbonyl chloride, (3S, 6R)-3-(tert-butoxycarbonyl)aminohexahydro-6-(cyclopentanecarbonyl)oxy-2H-azepin-2-one is obtained. Employing the compound above in place of compound 1g), and following essentially the procedure of Example 1h), 1i) and the last step of Example 1, the title compound is obtained. $H_2O$ solubility=18 mg/mL; mp 75–76° C.; $^1$H NMR (DMSO): δ 7.81 (d, J=6.47 Hz, 1H), 7.76 (t, J=6.07 Hz, 1H), 5.64 (d, J=15.77 Hz,1H), 5.34 (dd, J=15.76 Hz and 2.84 Hz, 1H), 4.80 (s, 1H), 4.57 (d, J=4.73 Hz,1H), 4.48 (d, J=6.94 Hz, 1H), 4.45 (m, 1H), 4.36 (d, J=5.83 Hz, 1H), 3.98 (m, 1H), 3.71 (d, J=6.94 Hz 1H), 3.57 (td, J=6.78 Hz and 2.68 Hz, 1H), 3.52 (dd, J=15.61 Hz and 4.57 Hz, 1H), 3.34 (td, 6.15 Hz and 2.84 Hz, 1H), 3.32 (s, 3H), 3.23 (m, 1H), 2.72 (m, 1H), 2.50 (m, 1H), 1.93 (m, 2H), 1.80 (m, 2H), 1.73 (m, 3H), 1.61 (m, 2H), 1.53 (m, 2H), 0.98 (s, 9H); $^{13}$C NMR (DMSO): δ 174.75, 173.56, 169.73, 141.69, 125.32, 81.60, 72.82, 72.54, 70.80, 67.20, 57.31, 50.95, 43.21, 32.44, 31.31, 29.45, 29.38, 25.30, 25.23.

EXAMPLE 3

(2R, 3R, 4S, 5R, 6E)-3,4,5-trihydroxy-2-methoxy-8,8-dimethyl-N-[(3S, 6R)-hexahydro-2-oxo-6-(cycloheptylcarbonyl)oxy-2H-azepin-3-yl]non-6-enamide.

Following essentially the procedure of Example 1g) and using in place of cyclohexane-carbonyl chloride, an approximately equivalent amount of a mixture consisting of: cycloheptanecarboxylic acid, 1-(3-dimethylaminopropyl)-3-ethylcarbodiimide hydrochloride and 4-dimethylaminopyridine; (3S, 6R)-3-(tert-butoxycarbonyl)aminohexahydro-6-(cycloheptane-carbonyl) oxy-2H-azepin-2-one is obtained. Employing the compound above in place of compound 1g), and following essentially the procedure of Example 1h),₁i) and the last step of Example 1, the title compound is obtained: mp 84–86° C.; $^1$H NMR ($CDCl_3$): δ 8.00 (d, J=6.3 Hz, 1H), 5.93 (t, J=5.52 Hz, 1H), 5.83 (d, J=15.77 Hz, 1H), 5.42 ( dd, J=15.7 Hz and 7.26 Hz, 1H), 4.93 (m, 1H), 4.55 (dd, J=9.46 Hz and 6.31 Hz, 1H), 4.23 (m, 2H), 3.82 (m,2H), 3.61 (t, J=6.14 Hz, 1H), 3.57 (m, 1H), 3.55 (s, 3H), 3.49 (dd, J=15.60 Hz and 5.20 Hz, 1H), 3.29 (d, J=7.25 Hz,1H), 3.10 (s, 1H), 2.50 (m, 1H), 2.17 (m, 1H), 1.95 (m, 4H), 1.70 (m, 1H), 1.65 (m, 2H), 1.55 (m, 4H), 1.47 (m, 4H), 1.02 (s, 9H); $^{13}$C NMR ($CDCl_3$): δ 176.17, 174.07, 172.14, 145.75, 123.20, 81.08, 74.51, 72.76, 72.44, 66.79, 59.95, 51.67, 45.07, 43.36, 33.03, 31.95, 30.91, 30.84, 29.43, 28.24, 28.21, 26.26, 25.73.

EXAMPLE 4

(2R, 3R, 4S, 5R, 6E)-3,4,5-trihydroxy-2-methoxy-8,8-dimethyl-N-[(3S, 6R)-hexahydro-2-oxo-6-(1-oxo-3-phenylpropoxy)-2H-azepin-3-yl]non-6-enamide.

Following essentially the procedure of Example 1 g) and using in place of cyclohexane-carbonyl chloride, an approximately equivalent amount of 3-phenylpropionyl chloride, (3S, 6R)-3-(tert-butoxycarbonyl)aminohexahydro-6-(1-oxo-3-phenylpropoxy)-2H-azepin-2-one is obtained. Employing the compound above in place of compound 1g), and following essentially the procedure of Example 1h), 1i) and the last step of Example 1, the title compound is obtained: $H_2O$ solubility=0.8 mg/mL; mp 75–77° C.; $^1$H NMR ($CDCl_3$) δ 7.96 (d, J=6.15 Hz,1H), 7.31 (t, J=7.25 Hz,2H), 7.23 (t, J=7.57 Hz, 1H), 7.20 (d, J=7.41 Hz, 2H), 5.82 (d, J=15.76 Hz,1 H), 5.62 (s, 1H), 5.41 (dd, J=15.76 Hz and 7.09 Hz, 1H), 4.92 (s, 1H), 4.49 (dd, J=9.46 Hz and 6.31 Hz, 1H), 4.22 (m, 2H), 3.80 (m, 2H), 3.60 (s, 1H), 3.52 (s, 3H), 3.37 (m,3H), 3.17 (s, 1H), 2.95 (t, J=7.57 Hz, 2H), 2.67 (t, J=7.72 Hz, 2H), 2.06 (d, J=11.98 Hz, 1H), 1.96 (t, J=12.77 Hz, 1H), 1.88 (s, 1H), 1.70 (m, 1H), 1.02 (s, 9H); $^{13}$C NMR ($CDCl_3$): δ 173.96, 172.05, 172.00 145.68, 140.08, 128.61, 128.42, 126.52, 123.21, 81.18, 74.46, 72.69, 72.50, 67.14, 59.83, 51.49, 43.22, 35.78, 33.02, 31.79, 31.07, 29.43, 25.58.

EXAMPLE 5

(2R, 3R, 4S, 5R, 6E)-3,4,5-trihydroxy-2-methoxy-8,8-dimethyl-N-[(3S, 6R)-hexahydro-2-oxo-6-(1 -oxo-3-[3-pyridyl]propoxy)-2H-azepin-3-yl]non-6-enamide.

Following essentially the procedure of Example 1g) and using in place of cyclohexane-carbonyl chloride, an approximately equivalent amount of a mixture consisting of: 3-(pyridyl) propionic acid, 1-(3-dimethylaminopropyl)-3-ethylcarbodiimide hydrochloride and 4-dimethylaminopyridine; (3S, 6R)-3-(tert-butoxycarbonyl) aminohexahydro-6-(1-oxo-3-[3-pyridyl]propoxy)-2H-azepin-2-one is obtained. Employing the compound above in place of compound 1g), and following essentially the procedure of Example 1h), 1i) and the last step of Example 1, the title compound is obtained. $^1$H NMR (CDCl$_3$) δ 8.46 (s, 2H), 7.97 (d, J=6.2 Hz, 1H), 7.53 (m, 1H), 7.23 (m, 1H), 5.88 (t, J=6.0 Hz, 1H), 5.81 (d, J=15.6 Hz, 1H), 5.4 (dd, J=15.6 and 7.3 Hz, 1H), 4.93 (m, 1H), 4.27 (s, 1H), 4.23–4.19 (m, 1H), 3.8 (m, 2H), 3.59 (d, J=5.2 Hz, 1H), 3.52 (s, 3H), 3.48 (m, 2H), 3.28 (s, 1H), 3.19 (s, 1H), 2.95 (t, J=7.3 Hz, 2H), 2.67 (t, J=7.3 Hz, 2H), 2.1–1.67 (m, 6H), 1.0 (s, 9H); $^{13}$C NMR (CDCl$_3$) δ 174.0, 172.0, 171.5, 149.7, 148.0, 145.7, 136.0, 135.5, 123.6, 123.2, 81.2, 74.5, 72.7, 72.5, 67.6, 59.8, 51.6, 43.3, 35.2, 33.0, 31.8, 29.4, 28.0, 25.5. HPLC: C-18 Novapac, 4.6×250 mm, 1.5 mL/min; solvent system: 25% MeCN/75% H$_2$O [isocratic]; retention time =13.7 min.

EXAMPLE 6

(2R, 3R, 4S, 5R, 6E)-3,4,5-Trihydroxy-2-Methoxy-8,8-Dimethyl-N-[(3S, 6R)-Hexahydro-2 -oxo-6-(cyclohexylmethylcarbonyl)oxy-2H-azepin-3-yl] non-6-enamide.

Following essentially the procedure of Example 1g) and using in place of cyclohexane-carbonyl chloride, an approximately equivalent amount of a mixture consisting of: cyclohexylacetic acid , 1-(3-dimethylaminopropyl)-3-ethylcarbodiimide hydrochloride and 4-dimethylaminopyridine; (3S, 6R)-3-(tert-butoxycarbonyl) aminohexahydro-6-(cyclohexylmethylcarbonyl) oxy-2H-azepin-2-one is obtained. Employing the compound above in place of compound 1g), and following essentially the procedure of Example 1h), 1i) and the last step of Example 1, the title compound is obtained. $^1$H NMR (CDCl$_3$) δ 7.98 (d, J=6.2, 1 H), 5.83–5.7 (m, 1H), 5.80 (d, J=15.6 Hz, 1 H), 4.94 (m, 1H), 4.52 (m, 1H), 4.2 (m, 2H), 3.78 (m, 2H), 3.6–3.48 (m, 3H), 3.52 (s, 3H), 3.23 (d, J=7.3 Hz, 1 H), 3.06 (m,1H), 2.80 (d, J=7 Hz, 2H), 2.13–1.63 (m, 12H), 1.30–0.85 (m, 5H), 1.0 (s, 9H); $^{13}$C NMR (CDCl$_3$) δ 174.0, 172.3, 172.2, 145.7, 123.3, 81.1, 74.5, 72.8, 72.5, 67.0, 60.0, 51.7, 43.5, 42.1, 35.0, 33.0, 32.0, 29.5, 26.1, 26.0, 25.7. HPLC: C-18 Novapac, 4.6×250 mm, 1.5 mL/min; solvent system: 40% MeCN/60% H$_2$O [isocratic]; retention time =11.5 min.

EXAMPLE 7

(2R, 3R, 4S, 5R, 6E)-3,4,5-trihydroxy-2-methoxy-8, 8-dimethyl-N-[(3S, 6R)-hexahydro-2-oxo-6-(1 -oxo-2-phenylethoxy)-2H-azepin-3-yl]non-6-enamide.

Following essentially the procedure of Example 1g) and using in place of cyclohexane-carbonyl chloride, an approximately equivalent amount of a mixture consisting of: phenylacetic acid, 1-(3-dimethylaminopropyl)-3-ethylcarbodiimide hydrochloride and 4-dimethylaminopyridine; (3S, 6R)-3-(tert-butoxycarbonyl) aminohexahydro-6-(1-oxo-2-phenylethoxy)-2H-azepin-2-one is obtained. Employing the compound above in place of compound 1g), and following essentially the procedure of Example 1h), 1i) and the last step of Example 1, the title compound is obtained. $^1$H NMR (CDCl$_3$) δ 7.96 (d, J=6.2, 1H), 7.28 (m, 5H), 5.80 (d, J=15.8 Hz, 1H), 5.68 (t, J=6.4 Hz, 1H), 5.39 (dd, J=15.8 and 7.3 Hz, 1H), 4.93 (m, 1H), 4.53–4.47 (m, 1H), 4.22–4.18 (m, 2H), 3.60–3.56 (m, 2H), 3.52 (s, 3H), 3.48–3.38 (m, 2H), 3.27 (d, J=6.6 Hz, 1H), 3.08 (s, 1H), 2.15–1.67 (m, 5H), 1.0 (s, 9H); $^{13}$C NMR (CDCl$_3$) δ 173.9, 172.1, 170.8, 145.8, 133.6, 129.2, 128.8, 127.4, 123.2, 81.1, 74.5, 72.7, 72.4, 67.6, 59.9, 51.6, 43.2, 41.5, 33.0, 31.8, 29.4, 25.5. HPLC: C-18 Novapac, 4.6×250 mm, 1.5 mL/min; solvent system: 10–100% MeCN/H$_2$O [>20 min gradient]; retention time=12.2 min.

EXAMPLE 8

(2R, 3R, 4S, 5R, 6E)-3,4,5-trihydroxy-2-methoxy-8, 8-dimethyl-N-[(3S, 6R)-Hexahydro-2-oxo-6-(1-oxo-2-[3,4-dichlorophenyl]ethoxy)-2H-azepin-3-yl]non-6-enamide.

Following essentially the procedure of Example 1g) and using in place of cyclohexane-carbonyl chloride, an approximately equivalent amount of a mixture consisting of: 3,4-dichlorophenylacetic acid, 1-(3-dimethylaminopropyl)-3-ethylcarbodiimide hydrochloride and 4-dimethylaminopyridine; (3S, 6R)-3-(tert-butoxycarbonyl) aminohexahydro-6-(1-oxo-2-[3,4-dichlorophenyl]ethoxy)-2H-azepin-2-one is obtained. Employing the compound above in place of compound 1g), and following essentially the procedure of Example 1h), 1i) and the last step of Example 1, the title compound is obtained; mp 132–136 ° C.; $_1$H NMR (CDC1$_3$) δ 8.00 (d, J=6 Hz, 1H), 7.51 (s, 1H), 7.41 (m, 2H), 7.16 (dd, J=3 Hz and 9 Hz, 1H), 5.77 (d, J=16 Hz, 1H), 5.42 (dd, J=8 Hz and 16 Hz, 1H), 4.93 (d, J=3 Hz, 1H), 4.55 (q, J=6 Hz, 1H), 4.19 (m, 1H), 3.83 (m, 3H), 3.63 (d, J=6 Hz, 3H), 3.48 (m, 6H), 3.39 (s, 1H), 2.13 (d, J=16 Hz, 1H), 2.00 (m, 2H), 1.77 (q, J=12 Hz, 1H), 1.03 (s, 9H); 13C NMR (CDCl$_3$) δ 169.1, 144.2, 133.5, 131.5,130.9, 130.8, 129.8, 128.5, 123.4, 81.3, 73.6, 72.2, 71.7, 67.6, 58.4, 50.8, 49.3, 42.0, 32.3, 31.1, 30.7, 28.8, 24.8.

EXAMPLE 9

(2R, 3R, 4S, 5R, 6E)-3,4,5trihydroxy-2-methoxy-8, 8-dimethyl-N-[(3S, 6R)-hexahydro-2-oxo-6-(1 -oxo-2-[4-methoxyphenyl]ethoxy)-2H-azepin-3-yl]non-6-enamide.

a) Preparation of (3S, 6R)-3-(tert-butoxycarbonyl) aminohexahydro-6-t-butyl-dimethylsilyloxy-2H-azepin-2-one.

(3S, 6R)-3-(tert-butoxycarbonyl)aminohexahydro-6-hydroxy-2H-azepin-2-one (25g, 102 mmol), tert-butyldimethylsilyl chloride (23.16g, 153 mmol), and imidazole (10.45 g, 153 mmol) are combined with 60 mL of DMF. The reaction is stirred at room temperature overnight. The mixture is diluted with 1 L of water. The resulting mixture is extracted with a 1:1 (2×200 mL) mixture of ethyl acetate and hexane. All organic layers are combined, washed with brine solution, dried with NaSO$_4$, and concentrated. The residue is purified by recrystallization with ethyl acetate/ hexane to give 28.5g (78%) of (3S, 6R)-3-(tert-butoxycarbonyl) aminohexahydro-6-tert-butyldimethylsilyloxy-2H-azepin-2-one as a white solid, mp 65–66 ° C.; $^1$H NMR (CDCl$_3$) δ 5.86 (d, J=6 Hz, 1H), 5.58 (t, J=6 Hz, 1H), 4.18 (m, 1H), 3.91 (s, 1H), 3.35 (dd, J=6 Hz and 16 Hz, 1H), 3.07 (m, 1H), 1.80 (m, 4H), 1.40 (s, 9H), 0.83 (s, 9H), 0.004 (s, 6H).

b) Preparation of (3S, 6R)-3-aminohexahydro-6-tert-butyldimethylsilyloxy-2H-azepin-2-One.

(3S, 6R)-3-(tert-butoxycarbonyl)aminohexahydro-6-tert-butyldimethylsilyloxy-2H-azepin-2-one (8.0 g, 22 mmol) is dissolved in 40 mL of $CH_2Cl_2$ and cooled to −78 °C. Trimethylsilyl iodide (3.5 mL, 24.5 mmol) is added slowly. The mixture is allowed to react at −78 °C. for 30 min. The reaction is warmed to 0°C. and stirred for 15 min. The solution turned yellow. The reaction is quenched with $NH_4HCO_3$ (3.43g, 44 mmol) dissolved in 30 mL of $CH_3OH$, and 15 mL water. The mixture is concentrated and chromatographed with 95:5 mixture of $CH_2Cl_2$ and methanol to yield 5.45 g (96%) of (3S, 6R)-3-aminohexahydro-6-tert-butyl-dimethylsilyloxy-2H-azepin-2-one as a white solid: $^1$H NMR (CDCl$_3$) δ 5.61 (s, 1H), 3.88 (s, 1H), 3.42 (d, J=8 Hz, 1H), 3.32 (dd, J=6 Hz and 16 Hz, 1H), 3.06 (m, 1H), 1.87 (m, 2H), 1.76 (m, 1H), 1.65 (s, 3H), 0.83 (s, 9H), 0.001 (s, 6H).

c) Preparation of (2R, 3R, 4S, 5R, 6E)-3,5-(methylethylidene)-3,4,5-trihydroxy-2-methoxy-8,8-dimethyl-N-[(3S, 6R)-hexahydro-2-oxo-6-tert-butyidimethylsilyloxy-2H-azepin-3-yl]non-6-enamide.

(3S, 6R)-3-aminohexahydro-6-tert-butyidimethylsilyloxy-2H-azepin-2-one (5.45g, 21 mmol), (6E)-6,7,8,9-tetradeoxy-8,8-dimethyl-2-O-methyl-3,5-O-(1-methylethylidene)-gulo-non-6-enonic acid lactone (3.0 g, 11 mmol), and diisopropylethylamine (4.6 mL, 26 mmol) are combined with 30 mL of isopropanol at room temperature. The mixture is heated to reflux overnight. The mixture is cooled to room temperature and concentrated. The residue is chromatographed with 98:2 mixture of $CH_2Cl_2$ and methanol to yield 2.53 g (42%) of (2R, 3R, 4S, 5R, 6E)-3,5-(methylethylidene)-3,4,5trihydroxy-2-methoxy-8,8-dimethyl-N-[(3S, 6R)-hexahydro-2-oxo-6-tert-butyidimethylsilyloxy-2H-azepin-3-yl]non-6-enamide (42%) as a white solid: $^1$H NMR (CDCl$_3$) δ 7.53 (d, J=6 Hz, 1H), 5.72 (d, J=16 Hz, 1H), 5.47 (dd, J=6 Hz and 16 Hz, 1H), 4.47 (m, 1H), 4.22 (d, J=6 Hz, 1H), 4.03 (d, J=8 Hz, 1H), 3.91 (m, 1H), 3.82 (d, J=7 Hz, 1H), 3.48 (d, J=9 Hz, 1H), 3.43 (s, 3H), 3.35 (d, J=6 Hz, 1H), 3.09 (m. 1H), 2.77 (d, J=9 Hz, 1H), 1.83 (m, 2H), 1.77 (m, 2H), 1.41 (d, J=6 Hz, 6H), 0.97 (s, 9H), 0.83 (s, 9H), 0.005 (s, 6H); $^{13}$C NMR (CDCl$_3$) δ 172.2, 169.6, 148.3, 145.3, 121.5, 108.8, 99.6, 81.4, 80.5, 79.2, 78.2, 74.4, 73.1, 69.1, 67.9, 65.8, 59.2, 56.4, 51.7, 36.8, 36.5, 33.1, 29.6, 29.4, 19.1.

d) Preparation of (2R, 3R, 4S, 5R, 6E)-3,5-(methylethylidene)-3,4,5-trihydroxy-2-methoxy-8,8-dimethyl-N-[(3S, 6R)-hexahydro-2-oxo-6-hydroxy-2H-azepin-3-yl]non-6-enamide.

(2R, 3R, 4S, 5R, 6E)-3,5-(methylethylidene)-3,4,5-trihydroxy-2-methoxy-8,8-dimethyl-N-[(3S, 6R)-hexahydro-2-oxo-6-tert-butydimethylsilyloxy-2H-azepin-3-yl]non-6-enamide (2.5 g, 4.6 mmol) is dissolved in 30 mL of THF. 1.0M in THF solution of tetrabutylammonium fluoride (13.8 mL, 14 mmol) is added at room temperature and stirred for 3 hrs. The mixture is concentrated and chromatographed with 95:5 mixture of $CH_2Cl_2$ and methanol to give 1.8 g (91%) of (2R, 3R, 4S, 5R, 6E)-3,5-(methylethylidene)-3,4,5-trihydroxy-2-methoxy-8,8-dimethyl-N-[(3S, 6R)-hexahydro-2-oxo-6-hydroxy-2H-azepin-3-yl]non-6-enamide as a white solid: $^1$H NMR (CDCl$_3$) δ 7.61 (d, J=6 Hz, 1H), 6.45 (t, J=6 Hz, 1H), 5.77 (d, J=6 Hz, 1H), 5.52 (dd, J=6 Hz, and 16 Hz, 1H), 4.56 (m, 1H), 4.28 (d, J=6 Hz, 1H), 4.06 (d, J=8 Hz, 1H), 4.00 (m, 1 H), 3.91 (d, J=8 Hz, 1 H), 3.54 (m, 1 H), 3.47 (s, 3H), 3.35 (m, 2H), 3.08 (d, J=8 Hz, 1H), 2.76 (d, J=6 Hz, 1), 2.02 (m, 2H), 1.83 (m, 2H), 1.45 (s, 6H), 1.03 (s, 9H); $^{13}$C NMR (CDCl$_3$) δ 175.1, 169.7, 145.3, 121.5, 99.7, 83.1, 80.6, 74.5, 73.2, 65.8, 64.6, 59.1, 51.8, 45.9, 34.5, 33.1, 29.5, 29.3, 25.1, 19.1, 13.7.

e) Preparation of (2R, 3R, 4S, 5R, 6E)-3,5-(methylethylidene)-3,4,5-trihydroxy-2-methoxy-8,8-dimethyl-N-[(3S, 6R)-hexahydro-2-oxo-6-(1-oxo-2-[4-methoxyphenyl]ethoxy)-2H-azapan-3-yl]non-6-enamide.

4-Methoxyphenylacetic acid (0.35 g, 2.1 mmol), 1-(3-dimethylaminopropyl)-3-ethylcarbo-diimide hydrochloride (0.42 g, 2.1 mmol), and DMAP (0.17 g, 1.4 mmol) are combined with 30 mL of $CH_2Cl_2$ and stirred at room temperature for 30 min. (2R, 3R, 4S, 5R, 6E)-3,5-(methylethylidene)-3,4,5-trihydroxy-2-methoxy-8,8-dimethyl-N-[(3S, 6R)-hexahydro-2-oxo-6-hydroxy-2H-azepin-3-yl]non-6-enamide (0.6 g, 1.4 mmol) is added to the mixture and stirred overnight at room temperature. The mixture is concentrated. The residue is chromato-graphed with 98:2 mixture of $CH_2Cl_2$ and methanol to give 0.644g (80%) of (2R, 3R, 4S, 5R, 6E)-3,5-(methylethylidene)-3,4,5-trihydroxy-2-methoxy-8,8-dimethyl-N-[(3S, 6R)-hexahydro-2-oxo-6-(1-oxo-2 -[4-methoxyphenyl]ethoxy)-2H-azapan-3-yl]non-6-enamide as a white solid: $^1$H NMR (CDCl$_3$) δ 7.56 (d, J=6 Hz, 1H), 7.18 (d, J=8 Hz, 2H), 6.86 (d, J=8 Hz, 2H), 5.78 (d, J=16 Hz, 1H), 5.62 (t, J=6 Hz, 1H), 5.52 (dd, J=6 Hz and 16 Hz, 1H), 4.93 (s, 1H), 4.58 (m, 1H), 4.28 (d, J=12 Hz, 1H), 4.06 (d, J=8 Hz, 1H), 3.88 (d, J=7 Hz, 1H), 3.80 (s, 3H), 3.56 (s, 2H), 3.48 (s, 5H), 2.82 (d, J=11 Hz, 1H), 2.05 (m, 3H), 1.71 (s, 2H), 1.42 (d, J=6 Hz, 6H), 1.03 (s, 9H); $^{13}$C NMR (CDCl$_3$) δ 174.3, 171.1, 169.7, 158.9, 145.3, 130.2, 125.7, 121.6, 114.2, 99.7, 80.6, 74.5, 73.3, 67.7, 65.8, 59.3, 55.3, 51.7, 43.3, 40.6, 33.1, 31.8, 31.4, 29.4, 25.8, 19.1.

f) Preparation of the title compound.

30 mL solution of (3:3:2) TFA, THF, and water at 0 °C. is added to a flask containing (2R, 3R, 4S, 5R, 6E)-3,5-(methylethylidene)-3,4,5-trihydroxy-2-methoxy-8,8-dimethyl-N-[(3S, 6R)-hexahydro-2-oxo-6-(1 -oxo-2-[4-methoxyphenyl]ethoxy)-2H-azapan-3-yl]non-6-enamide (0.64g, 1.1 mmol). The mixture is allow to react at 0 °C. for 30 min. The mixture is evaporated to dryness under high vacuum. The residue is neutralized with a solution $NH_4HCO_3$ (1.2 g in 20 mL of water). The mixture is evaporated to dryness under high vacuum. The residue is chromatographed with a 95:5 mixture of $CH_2Cl_2$ and methanol to yield 0.35 g (60%) of the title compound as a white solid: $^1$H NMR (CDCl$_3$) δ 7.98 (d, J=6 Hz, 1H), 7.18 (d, J=9 Hz, 2H), 6.87 (d, J=9 Hz, 2H), 5.83 (d, J=16 Hz, 1H), 5.72 (t, J=6 Hz, 1H), 5.42 (dd, J=8 Hz and 16 Hz, 1H), 4.93 (d, J=3 Hz, 1H), 4.53 (m, 1H), 4.23 (t, J=6 Hz, 2H), 3.81 (m, 2H), 3.80 (s, 3H), 3.61 (t, J=5 Hz, 1H), 3.57 (s, 2H), 3.54 (s, 3H), 3.47 (m, 1H), 3.30 (d, J=7 Hz, 1H), 3.12 (s, 1H), 2.16 (d, J=16 Hz, 1H), 1.99 (m, 2H), 1.82 (m, 1H), 1.72 (s, 1H), 1.04 (s, 9H); $^{13}$C NMR (CDCl$_3$) δ 173.8, 172.2, 171.1, 158.9, 145.8, 130.2, 125.6, 123.2, 114.2, 81.0, 74.5, 72.8, 72.4, 67.5, 60.0, 55.3, 51.6, 43.2, 40.6, 33.0, 31.8, 31.3, 29.4, 25.6.

EXAMPLE 10

(2R, 3R, 4S, 5R, 6E)-3,4,5-trihydroxy-2-methoxy-8,8-dimethyl-N-[(3S, 6R)-hexahydro-2-oxo-6-([4-n-decyloxyphenyl]carbonyl)oxy-2H-azepin-3-yl]non-6-enamide.

Following essentially the procedure of Example 9e) and using in place of 4-methoxy-phenylacetic acid, an approximately equivalent amount of 4-decyloxybenzoic acid, (2R, 3R, 4S, 5R, 6E)-3,5-(methylethylidene)-3,4,5-trihydroxy-2-methoxy-8,8-dimethyl-N-[(3S, 6R)-hexahydro-2-oxo-6-([4-n-decyloxyphenyl]carbonyl)oxy-2H-azepin-3-yl]non-6-enamide is obtained. Employing the compound above in place of compound 9e), and following essentially the procedure of the last step of Example 9, the title compound is obtained as a solid with mp 70–74° C; $^1$H NMR (CDCl) δ 8.06 (d, J=6 Hz, 1H), 7.96 (d, J=9 Hz, 2H), 6.90 (d, J=9 Hz, 2H), 6.05 (t, J=6 Hz, 1H), 5.80 (d, J=15 Hz, 1H), 5.44 (dd, J=7 Hz and 15 Hz, 1H), 5.20 (m, 1H), 4.63 (m, 1H), 4.25 (t, J=6 Hz, 1H), 4.02 (t, J=6 Hz, 2H), 3.84 (dd, J=7 Hz and 13 Hz, 2H), 3.69 (m, 1H), 3.62 (m, 2H), 3.38 (d, J=5 Hz, 1H), 3.56 (s, 3H), 3.33 (s, 1H), 3.15 (s, 1H), 2.32 (d, J=12 Hz, 1H), 2.13 (t, J=12 Hz, 1H), 2.01 (m, 2H), 1.82 (m, 2H), 1.48 (m, 2H), 1.30 (m, 12H), 1.05 (s, 9H), 0.94 (t, J=6 Hz, 3H); $^{13}$C NMR (CDCl$_3$) δ 174.1, 172.1, 165.2, 163.4,145.7, 131.7, 123.2, 121.6, 114.2, 81.1, 74.5, 72.7, 72.4, 68.3, 67.2, 59.9, 51.7, 43.6, 33.0, 32.1, 31.9, 29.5, 29.4, 29.3, 29.2, 29.0, 25.9, 25.9, 22.6, 14.1.

EXAMPLE 11

(2R, 3R, 4S, 5R, 6E)-3,4,5-trihydroxy-2-methoxy-8,8-dimethyl-N-[(3S, 6R)-hexahydro-2-oxo-6-(1-oxo-3-phenyl-2-propenoxy)-2H-azepin-3-yl]non-6-enamide.

Following essentially the procedure of Example 1g) and using in place of cyclohexane-carbonyl chloride, an approximately equivalent amount of cinnamoyl chloride, (3S, 6R)-3-(tert-butoxycarbonyl) aminohexahydro-6-(1-oxo-3-phenyl-2-propenoxy)-2H-azepin-2-one is obtained. Employing the compound above in place of compound 1 g), and following essentially the procedure of Example 1h), 1i) and the last step of Example 1, the title compound is obtained as a solid, mp 83–85° C.; $^1$H NMR (DMSO): δ 8.03 (m, 1H), 7.71 (d, J =16 Hz, 1H), 7.54 (m, 2H), 7.41 (m, 2H), 6.45 (d, J =16Hz, 1H), 5.97 (m, 1H), 5.81 (d, J=16 Hz, 1H), 5.45 (dd, J=16 and 8 Hz, 1H), 5.09 (m, 1H), 4.58 (m, 1H), 4.22 (m, 2H), 3.81 (m, 2H), 3.62 (m, 4H), 3.54 (s, 3H), 3.30 (d, J=8 Hz, 1H), 3.10 (s, 1H), 2.25 (m, 1H), 2.00 (m, 3H), 1.02 (s, 9H); $^{13}$C NMR (DMSO): δ 174.10, 172.15, 166.01, 145.91, 145.75, 134.03, 130.70, 129.00, 128.22, 123.20, 117.34, 81.10, 74.50, 72.76, 72.46, 67.29, 59.93, 51.67, 43.51, 33.03, 32.00, 29.43, 25.75.

EXAMPLE 12

(2R, 3R, 4S, 5R, 6E)-3,4,5-trihydroxy-2-methoxy-8,8-dimethyl-N-[(3S, 6R)-hexahydro-2-oxo-6-([4-N-decylphenyl]carbonyl)oxy-2H-azepin-3-yl]non-6-enamide.

Following essentially the procedure of Example 9e) and using in place of 4-methoxy-phenylacetic acid, an approximately equivalent amount of 4-decylbenzoic acid, (2R, 3R, 4S, 5R, 6E)-3,5-(methylethylidene)-3,4,5-trihydroxy-2-methoxy-8,8-dimethyl-N-[(3S, 6R)-hexahydro-2-oxo-6-([4-n-decylphenyl]carbonyl)oxy-2H-azepin-3-yl]non-6-enamide is obtained. Employing the compound above in place of compound 9e), and following essentially the procedure of the last step of Example 9, the title compound is obtained: mp 60–64° C.; $^1$H NMR (CDCl) δ 8.06 (d, J=6 Hz, 1 H), 7.94 (d, J=8 Hz, 2H), 7.26 (d, J=8 Hz, 2H), 6.10 (t, J=7 Hz, 1H), 5.85 (d, J=16 Hz, 1H), 5.45 (dd, J=8 Hz and 16 Hz, 1H), 5.22 (d, J=3 Hz, 1 H), 4.64 (dd, J=6 Hz and 8 Hz, 1 H), 4.25 (t, J=6 Hz, 2H), 3.84 (dd, J=6 Hz and 11 Hz, 2H), 3.69 (t, J=7 Hz, 1H), 3.63 (dd, J=5 Hz and 8 Hz,2H), 3.56 (s, 3H), 2.68 (t, J=8 Hz, 2H), 2.34 (d, J=13 Hz, 1H), 2.14 (t, J=12 Hz, 1H), 2.04 (t, J=11 Hz, 1H), 1.96 (t, J=3 Hz, 11H), 1.63 (m, 2H), 1.32 (m, 18H), 1.82 (m, 2H), 1.05 (s, 9H), 0.90 (t, J=7 Hz, 3H); $^{13}$C NMR (CDCl$_3$) δ 174.1, 172.1, 165.5, 149.3, 145.7, 129.7, 128.6, 127.0, 123.2, 81.1, 74.5, 72.7, 72.4, 67.4, 59.9, 51.7, 43.5, 36.0, 33.0, 32.1, 31.9, 31.1, 29.6, 29.5, 29.4, 29.3, 29.2, 25.9, 22.6, 14.1.

EXAMPLE 13

(2R, 3R, 4S, 5R, 6E)-3,4,5-trihydroxy-2-methoxy-8,8-dimethyl-N-[(3S, 6R)-hexahydro-2-oxo-6-(1 -oxo-3-[3-thiophenyl]ethoxy)-2H-azepin-3-yl]non-6-enamide.

Following essentially the procedure of Example 1g) and using in place of cyclohexane-carbonyl chloride, an approximately equivalent amount of a mixture consisting of: 3-thiopheneacetic acid, 1-(3-dimethylaminopropyl)-3-ethylcarbodiimide hydrochloride and 4-dimethylaminopyridine; (3S, 6R)-3-(tert-butoxycarbonyl) aminohexahydro-6-(1-oxo-3-[3-thiophenyl]ethoxy)-2H-azepin-2-one is obtained. Employing the compound above in place of compound 1g), and following essentially the procedure of Example 1h), 1i) and the last step of Example 1, the title compound is obtained: hplc (C-18 Novapac, 4.6×250 mm, 1.5 mL/min) solvent system: 35% MeCN/65% H$_2$O [isocratic]; Retention Time =7.89 min. $^1$H NMR (CDCl$_3$) δ 7.97 (d, J=6 Hz,1 H), 7.30 (m, 1H), 7.14 (m, 1H), 7.00 (m, 1H), 5.83 (m, 1H), 5.81 (d, J=16 Hz, 1H), 5.40 (dd, J=7 Hz and 16 Hz, 1H), 4.90 (m, 1H), 4.45 (m, 1H), 4.15 (m, 1H), 3.75 (m, 2H), 3.66 (s, 2H), 3.57 (s, 3H), 3.40 (m, 2H), 3.32 (d, J=7 Hz, 1H), 3.12 (s, 1H), 1.7 (m, 4H), 1.01 (s, 9H); $^{13}$C NMR (CDCl$_3$) δ 174.0, 172.1, 170.3, 145.7, 133.1, 126.2, 123.3, 123.1, 81.2, 74.5, 72.8, 72.5, 67.8, 59.9, 51.6, 43.2, 36.0, 33.0, 31.8, 29.5, 25.6.

EXAMPLE 14

(2R, 3R, 4S, 5R, 6E)-3,4,5-trihydroxy-2-methoxy-8,8-dimethyl-N-[(3S, 6R)-hexahydro-2-oxo6-(1-oxo-3-[3-indolyl]ethoxy)-2H-azepin-3-yl]non-6-enamide.

Following essentially the procedure of Example 1g) and using in place of cyclohexane-carbonyl chloride, an approximately equivalent amount of a mixture consisting of: 3-indoleacetic acid, 1-(3-dimethylaminopropyl)-3-ethylcarbodiimide hydrochloride and 4-dimethylaminopyridine; (3S, 6R)-3-(tert-butoxycarbonyl) aminohexahydro-6-(1-oxo-3-[3-indolyl]ethoxy)-2H-azepin-2-one is obtained. Employing the compound above in place of compound 1g), and following essentially the procedure of Example 1h), 1i) and the last step of Example 1, the title compound is obtained: hplc (C-18 Novapac, 4.6×250 mm, 1.5 mL/min) solvent system: 35% MeCN/65% H$_2$O [isocratic]; retention time =9.2 min. $^1$H NMR (CDCl$_3$) δ 8.47 (s, 1H), 7.90 (d, J=6 Hz, 1H), 7.55 (d, J=8 Hz, 1H), 7.36 (d, J=8 Hz, 1H), 7.20–7.05 (m, 3H), 5.81 (d, J=16 Hz, 1H), 5.75 (m, 1H), 5.37 (dd, J=8 Hz and 16 Hz, 1H), 4.8 (m, 1H), 4.45–4.30 (m, 2H), 4.25–4.15 (m, 1H), 3.9–3.7 (m, 4H), 3.65–3.55 (m, 1H), 3.50 (s, 3H), 3.45–3.30 (m, 1H), 3.25–3.10 (m, 2H), 2.15–2.00 (m, 1H), 2.00–1.60 (m, 4H), 0.99 (s, 9H); $^{13}$C NMR (CDCl$_3$) δ 173.9, 171.9, 145.7, 136.2, 127.1, 123.3, 123.3, 122.3, 119.8, 118.6, 111.5, 108.0, 81.6, 74.4, 72.7, 72.6, 67.5, 59.7, 51.5, 43.1, 33.0, 31.8, 31.6, 29.5, 25.6.

EXAMPLE 15

Infusion

The compound of Example 1 (15 mg) is dissolved in 98–100 % propylene glycol (1.0 ml). The solution is sterile filtered through a 0.22 microns pore size filter and charged to 1 ml ampoules. The filled ampoules are used for storage and shipment. The filled ampoules are stable for a period of at least 12 months at a temperature of 2 to 8° C. Prior to intravenous administration, the contents of an ampoule are added to 250 to 1000 ml of a 5% glucose solution in water-for-injection. The intravenous solution thus formed is stable for a period of 8 hours at room temperature.
Following are the corresponding structures of the compounds of Examples 1–14:
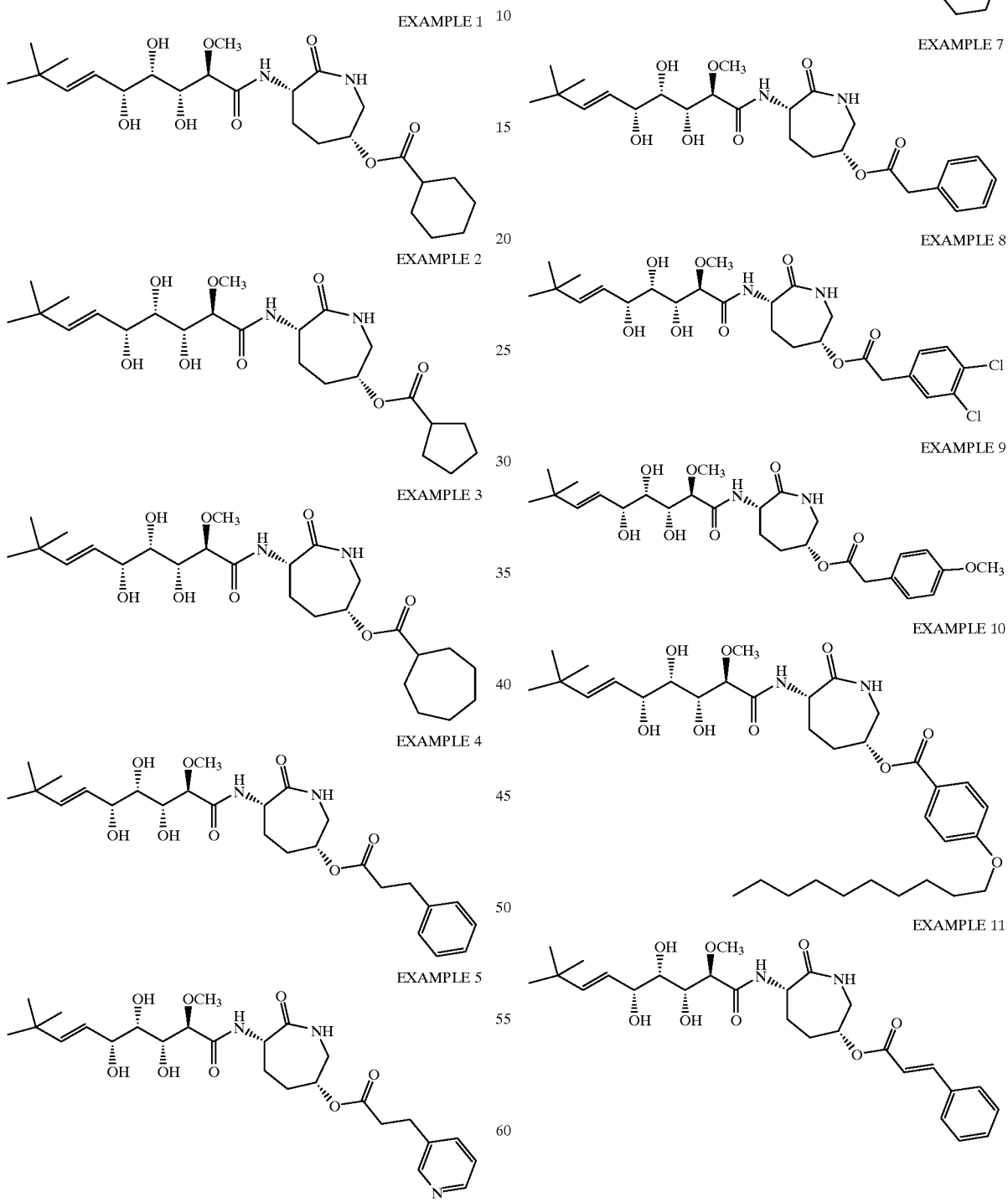

EXAMPLE 12

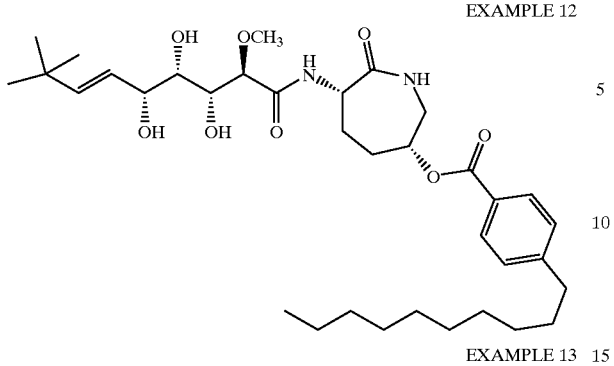

EXAMPLE 13

EXAMPLE 14

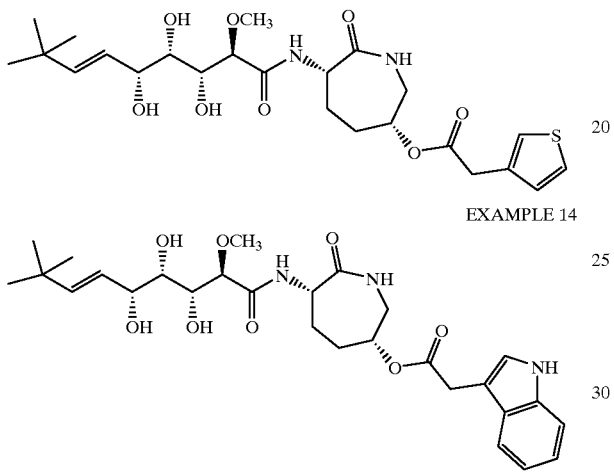

What is claimed is:

1. A compound of formula I:

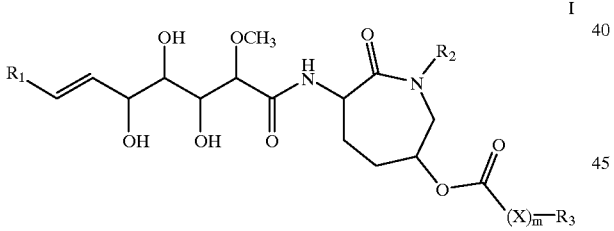

where $R_1$ is $(C_{1-6})$alkyl or $(C_{3-6})$cycloalkyl;

$R_2$ is hydrogen or $(C_{1-6})$alkyl;

X is $(C_{1-12})$ alkylene; $(C_{2-12})$ alkenylene; or $(C_{2-12})$ alkynylene;

m is 0 or 1; and $R_3$ is $(C_{3-8})$cycloalkyl; or an aromatic ring system selected from II, III, IV and V:

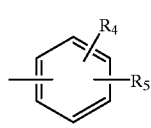

II

III

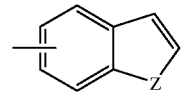

IV

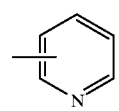

V where $R_4$ is hydrogen, chloro, or methoxy;

$R_5$ is hydrogen, chloro, $(C_{1-18})$alkyl or $(C_{1-18})$alkoxy; and Z is oxygen, sulfur, N—H, or N—CH$_3$;

or a pharmaceutically acceptable acid addition salt thereof, where possible.

2. A compound of formula I according to claim 1, where $R_1$ is $(C_{1-6})$ alkyl;

$R_2$ is hydrogen or $(C_{1-4})$ alkyl;

X is $(C_{1-6})$ alkylene or $(C_{2-6})$ alkenylene;

m is 0 or 1; and $R_3$ is $(C_{3-8})$cycloalkyl; or an aromatic ring system selected from II, III, IV and V where $R_4$ is hydrogen, chloro, or methoxy;

$R_5$ is hydrogen, chloro, $(C_{1-18})$alkyl or $(C_{1-18})$alkoxy; and Z is oxygen, sulfur, N—H, or N—CH$_3$;

or a pharmaceutically acceptable acid addition salt thereof, where possible.

3. A compound of formula I according to claim 2 where $R_1$ is i-propyl or t-butyl;

$R_2$ is hydrogen or methyl;

m is 0 or 1;

X is $(C_{1-6})$ alkylene; and $R_3$ is $(C_{5-7})$cycloalkyl; or an aromatic ring system selected from IIa and V:

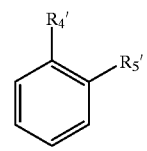

IIa

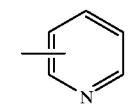

V where $R_4'$ is in the meta position and is hydrogen or chloro; and $R_5'$ is in the para position and is hydrogen, chloro, $(C_{1-18})$alkyl or $(C_{1-18})$alkoxy;

or a pharmaceuically acceptable acid addition salt thereof, where possible.

4. A compound of formula I according to claim 3 where $R_1$ is i-propyl or t-butyl;

$R_2$ is hydrogen or methyl;

m is 0 or 1;

X is methylene or ethylene; and $R_3$ is $(C_{5-7})$cycloalkyl, phenyl, 3,4-dichlorophenyl, 4-methoxyphenyl, 4-n-decylphenyl, 4-n-decyloxyphenyl or 3-pyridyl;

with the proviso that when m is 0, $R_3$ is $(C_{5-7})$cycloalkyl, 4-n-decylphenyl or 4-n-decyloxyphenyl;

or a pharmaceutically acceptable acid addition salt thereof, where possible.

5. A compound of formula I according to claim 1, selected from 3,4,5-trihydroxy-2-methoxy-8,8-dimethyl-N-[hexahydro-2-oxo-6-(cyclohexylcarbonyl)oxy-2H-azepin-3-yl]non-6-enamide, and 3,4,5-trihydroxy-2-methoxy-8,8-dimethyl-N-[hexahydro-2-oxo-6-(1-oxo-3-phenylpropoxy)-2H-azepin-3yl]non-6-enamide, or a pharmaceutically acceptable acid addition salt thereof.

6. A compound of formula I according to claim 1, selected from (2R, 3R, 4S, 5R, 6E)-3,4,5-trihydroxy-2-methoxy-8,8-dimethyl-N-[(3S, 6R)-hexahydro-2-oxo-6-(cyclohexylcarbonyl)oxy 2H-azepin-3-yl]non-6-enamide, and (2R, 3R, 4S, 5R, 6E)-3,4,5-trihydroxy-2-methoxy-8,8-dimethyl-N-[(3S, 6R)-hexahydro-2-oxo-6-(1-oxo-3-phenylpropoxy-2H-azepin-3-yl]non-6-enamide, or a pharmaceutically acceptable acid addition salt thereof.

7. A pharmaceutical composition comprising a compound of formula I according to claim 1, or a pharmaceutically acceptable acid addition salt thereof, where possible, together with a pharmaceutically acceptable carrier.

8. A pharmaceutical composition according to claim 7 comprising a therapeutically effective amount of a compound of formula I which is 3,4,5-trihydroxy-2-methoxy-8,8-dimethyl-N-[hexahydro-2-oxo-6-(cyclohexylcarbonyl)oxy-2H-azepin-3-yl]non-6-enamide.

9. A pharmaceutical composition according to claim 7 comprising a therapeutically effective amount of a compound of formula I which is 3,4,5-trihydroxy-2-methoxy-8,8-dimethyl-N-[hexahydro-2-oxo-6-(1oxo-3-phenylpropoxy)-2H-azepin-3-yl]non-6-enamide.

10. A process for preparing a caprolactam compound of formula I

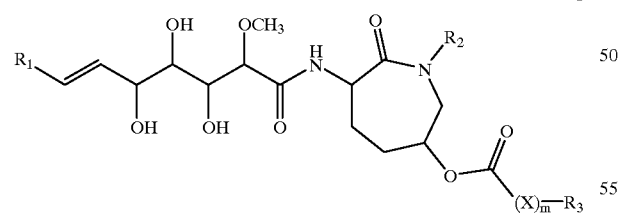

where $R_1$ is $(C_{1-6})$alkyl or $(C_{3-6})$cycloalkyl;

$R_2$ is hydrogen or $(C_{1-6})$alkyl;

X is $(C_{1-12})$ alkylene; $(C_{2-12})$ alkenylene; or $(C_{2-12})$ alkynylene;

m is 0 or 1; and $R_3$ is $(C_{3-8})$cycloalkyl; or an aromatic ring system selected from II, III, IV and V:

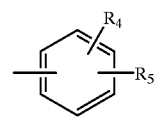

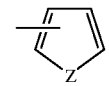

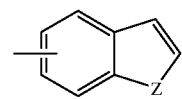

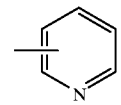

where $R_4$ is hydrogen, chloro, or methoxy;

$R_5$ is hydrogen, chloro, $(C_{1-18})$alkyl or $(C_{1-18})$alkoxy; and

Z is oxygen, sulfur, N—H, or N—$CH_3$;

or a pharmaceutically acceptable acid addition salt thereof, where possible, which process comprises, in a first step, acylating an aminocaprolactam compound of formula VI

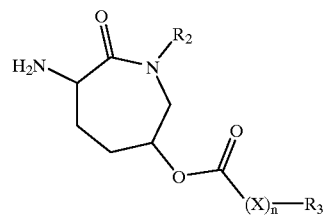

with a lactone compound of formula VII

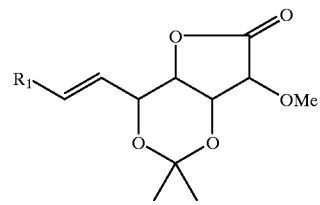

in the presence of a polar, organic solvent to obtain a diamide compound of formula VIII

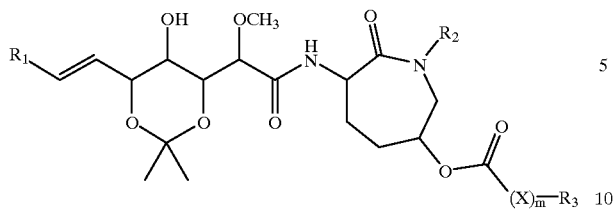 VIII where each of $R_1$, $R_2$, X, m and $R_3$ is as defined in claim 1 and, in a second step, hydrolyzing the diamide compound obtained in the first step by dissolving it in a mixture of solvents to obtain the desired caprolactam compound of formula I.

11. A process according to claim 10 wherein the acylation step is carried out in the presence of isopropanol at a temperature slightly below or at the reflux temperature of the isopropanol.

* * * * *